United States Patent [19]
Ni et al.

[11] Patent Number: 6,046,031
[45] Date of Patent: Apr. 4, 2000

[54] METALLOPROTEINASES

[75] Inventors: Jian Ni, Rockville; Steve Ruben, Olney; Laurie Brewer, Poolesville; Reiner Gentz, Silver Spring; Craig Rosen, Laytonsville, all of Md.

[73] Assignee: Human Genome Sciences, Inc., Rockville, Md.

[21] Appl. No.: 09/009,156

[22] Filed: Jan. 20, 1998

Related U.S. Application Data

[60] Provisional application No. 60/034,205, Jan. 21, 1997, provisional application No. 60/049,607, Jun. 13, 1997, and provisional application No. 60/054,541, Aug. 1, 1997.

[51] Int. Cl.[7] .................................................. C12P 21/06
[52] U.S. Cl. .................... 435/69.1; 435/69.3; 435/219; 435/226; 435/252.33; 435/325; 435/320.1; 536/23.1; 536/23.2; 536/23.5
[58] Field of Search .............................. 435/325, 252-33, 435/219, 226, 320.1, 69.1, 69.3; 536/23.2, 23.5, 23.1

[56] References Cited

FOREIGN PATENT DOCUMENTS

WO96/41624  12/1996  WIPO .

OTHER PUBLICATIONS

GenBank Accession No. Y08617 (Jun. 23, 1998).
GenBank Accession No. AA336600 (Apr. 21, 1997).
GenBank Accession No. AA336367 (Apr. 21, 1997).
Perry, A. C., Biochem. Journal, vol. 312:239–244 (1995).
GenBank Accession No. AA724715 (Jan. 8, 1998).
Gould, S. et al., Proc. Natl. Acad Sci., vol. 86: 1934–1938 (1989).
Hopp, T. P., et al., Proc. Natl Acad. Sci., vol. 78: 3824–3828 (1981).
Wolfsberg, T. G., et al., J. of Cell Biology, vol. 131:275–278 (1995).
Lunn, C., et al., FEBS Letters, vol. 400: 333–335 (1997).
Gupta, S., et al., Bioch. & Biophysical Research Comm., vol. 224:318–326 (1996).

*Primary Examiner*—Nashaat Nashed
*Attorney, Agent, or Firm*—A. Anders Brookes; Human Genome Sciences, Inc.

[57] ABSTRACT

The present invention relates to novel metalloproteinase-like proteins. In particular, isolated nucleic acid molecules are provided encoding the human TACE-like and matrilysin-like proteins. TACE-like and matrilysin-like polypeptides are also provided as are vectors, host cells and recombinant methods for producing the same. The invention further relates to screening methods for identifying agonists and antagonists of TACE-like and matrilysin-like activity. Also provided are diagnostic methods for detecting cancer and therapeutic methods for cancer and other disorders characterized by an over or under production of these metalloproteinases.

60 Claims, 9 Drawing Sheets

```
  1 ACGAGGCGCTCTGGCTGAGCCATGTTCCTTCTCCTCGCCCTCCTCACTGAGCTTGGAAGA  60
  1                       M  F  L  L  L  A  L  L  T  E  L  G  R  13

61 CTGCAAGCCCACGAAGGTTCTGAAGGAATATTTCTGCATGTCACAGTTCCACGGAAGATT 120
 14  L  Q  A  H  E  G  S  E  G  I  F  L  H  V  T  V  P  R  K  I  33

121 AAGTCAAATGACAGTGAAGTTTCAGAGAGGAAGATGATTTACATCATTACAATTGATGGA 180
 34  K  S  N  D  S  E  V  S  E  R  K  M  I  Y  I  I  T  I  D  G  53

181 CAACCTTACACTCTACATCTCGGAAAACAATCATTCTTACCCCAGAACTTTTTGGTTTAT 240
 54  Q  P  Y  T  L  H  L  G  K  Q  S  F  L  P  Q  N  F  L  V  Y  73

241 ACATATAATGAAACTGGATCTTTGCATTCTGTGTCTCCATATTTTATGATGCATTGCCAT 300
 74  T  Y  N  E  T  G  S  L  H  S  V  S  P  Y  F  M  M  H  C  H  93

301 TACCAAGGATATGCTGCCGAATTTCCAAATTCATTTGTGACACTCAGTATATGTTCTGGT 360
 94  Y  Q  G  Y  A  A  E  F  P  N  S  F  V  T  L  S  I  C  S  G  113

361 CTCAGGGGATTTCTCCAGTTTGAAAATATCAGTTATGGAATTGAACCAGTAGAATCTTCA 420
114  L  R  G  F  L  Q  F  E  N  I  S  Y  G  I  E  P  V  E  S  S  133

421 GCAAGATTTGAGCATATAATTTATCAAATGAAAAATAATGATCCAAATGTATCCATTTTA 480
134  A  R  F  E  H  I  I  Y  Q  M  K  N  N  D  P  N  V  S  I  L  153

481 GCAGTAAATTACAGTCATATTTGGCAGAAAGACCAGCCCTACAAAGTTCCTTTAAACTCA 540
154  A  V  N  Y  S  H  I  W  Q  K  D  Q  P  Y  K  V  P  L  N  S  173

541 CAGGTGACTGTCATCATTCTGATGTTATGACATACTAGAACATTGCCTGTGTAGTTTTCT 600
174  Q  V  T  V  I  I  L  M  L  *                                 182

601 TGTAAATCATGAAAGGAATTTAGTTAGCTGTTGAGTAGGAATATTAAATTTTATGTATTT 660

661 TTCTACCTTTAAATAAAACATTGAAACTTCAAAAAAAAAAAAA                  704
```

FIG. 1

```
  1 MFLLLALLTELGRLQAHEGSEGIFLHVTVPRKIKSNDSEV.SERKMIYII 49
    ||||.|||:||  ::|.  ...  .||:.|:| ||.|.|... .|:.::|:|
  1 mfiliviltgiggmhadinphkttiqttipekisssdaktdpeLnvvymi 50

50 TIDGQPYTLHLGKQSFLPQNFLVYTYNETGSLHSVSPYFMMHCHYQGYAA 99
    ||:|.|| :|| |||:|.. ::..|:..:  ||  ..  |.|:|.||.|
 51 tieghpyfvhlkkqsilssasfiLsydkndirhskpilvqmdcnyngyva 100

100 EFPNSFVTLSICSGLRGFLQFENISYGIEPVESSARFEHIIYQMKNNDPN 149
    ::|||:||||:||||||  :|:.||||||||:|.  .|  ||:  | .|.|
101 gi0nsivtisvcsqlrgtmqlknisygiepmeavsgfihkiyeeLfadtn 150

150 VSILAVNYSHIWQKDQPYKVPLNSQVTVIILML 182
    : :|.  |  .. |  ..: |.|. .|: |  :|  ::
151 i.lleendtyswfnse.yqvrkssektdfikif 181
```

FIG.2

```
  1  CCAAGCTCGAAATTAACCCTCACTAAAGGGAACAAAGGCACGAGCATGCAGCTCGTCATC   60
  1                                                  M  Q  L  V  I    5

61  TTAAGAGTTACTATCTTCTTGCCCTGGTGTTTCGCCGTTCCAGTGCCCCCTGCTGCAGAC  120
  6   L  R  V  T  I  F  L  P  W  C  F  A  V  P  V  P  P  A  A  D    25

121  CATAAAGGATGGGACTTTGTTGAGGGCTATTTCCATCAATTTTTCCTGACCGAGAAGGAG  180
 26   H  K  G  W  D  F  V  E  G  Y  F  H  Q  F  F  L  T  E  K  E    45

181  TCGCCACTCCTTACCCAGGAGACACAAACACAGCTCCTGCAACAATTCCATCGGAATGGG  240
 46   S  P  L  L  T  Q  E  T  Q  T  Q  L  L  Q  Q  F  H  R  N  G    65

241  ACAGACCTACTTGACATGCAGATGCATGCTCTGCTACACCAGCCCCACTGTGGGGTGCCT  300
 66   T  D  L  L  D  M  Q  M  H  A  L  L  H  Q  P  H  C  G  V  P    85

301  GATGGGTCCGACACCTCCATCTCGCCAGGAAGATGCAAGTGGAATAAGCACACTCTAACT  360
 86   D  G  S  D  T  S  I  S  P  G  R  C  K  W  N  K  H  T  L  T   105

361  TACAGGATTATCAATTACCCACATGATATGAAGCCATCCGCAGTGAAAGACAGTATATAT  420
106   Y  R  I  I  N  Y  P  H  D  M  K  P  S  A  V  K  D  S  I  Y   125

421  AATGCAGTTTCCATCTGGAGCAATGTGACCCCTTTGATATTCCAGCAAGTGCAGAATGGA  480
126   N  A  V  S  I  W  S  N  V  T  P  L  I  F  Q  Q  V  Q  N  G   145

481  GATGCAGACATCAAGGTTTCTTTCTGGCAGTGGGCCCATGAAGATGGTTGGCCCTTTGAT  540
146   D  A  D  I  K  V  S  F  W  Q  W  A  H  E  D  G  W  P  F  D   165

541  GGGCCAGGTGGTATCTTAGGCCATGCCTTTTTTACCAAATTCTGGAAATCCTGGAGTTGTC  600
166   G  P  G  G  I  L  G  H  A  F  L  P  N  S  G  N  P  G  V  V   185

601  CATTTTGACAAGAATGAACACTGGTCAGCTTCAGACACTGGATATAATCTGTTCCTGGTT  660
186   H  F  D  K  N  E  H  W  S  A  S  D  T  G  Y  N  L  F  L  V   205

661  GCAACTCATGAGATTGGGCATTCTTTGGGCCTGCAGCACTCTGGGAATCAGAGCTCCATA  720
206   A  T  H  E  I  G  H  S  L  G  L  Q  H  S  G  N  Q  S  S  I   225

721  ATGTACCCCACTTACTGGTATCACGACCCTAGAACCTTCCAGCTCAGTGCCGATGATATC  780
226   M  Y  P  T  Y  W  Y  H  D  P  R  T  F  Q  L  S  A  D  D  I   245

781  CAAAGGATCCAGCATTTGTATGGAGAAAAATGTTCATCTGACATACCTTAATGTTAGCAC  840
246   Q  R  I  Q  H  L  Y  G  E  K  C  S  S  D  I  *               261
```

FIG.4A

841 AGAGGACTTATTCAACCTGTCTTTCAGGGAGTTTATTGGAGGATCAAAGAACTGAAAGCA 900

901 CTAGAGCAGCCTTGGGGACTGCTAGGATGAAGCCCTAAAGAATGCAACCTAGTCAGGTTA 960

961 GCTGAACCGACACTCAAAACGCTACTGAGTCACAATAAAGATTGTTTTAAAGAGTAAAAA 1020

1021 AAAAAAAAAAAAAAA 1035

FIG.4B

```
  1 MQLVILRVTIFLPWCFAVPVPPAADHKG...WDFVEGYFHQFFLTEKESP  47
    |.|.:|  ...:||  ::|:|:|..|:  .:    |: .::|:..|:| :.|..
  1 MRLTVLCAVCLLPGSLALPLPQEAGGMSELQWEQAQDYLKRFYLYDSETK  50

48 .LLTQETQTQLLQQFHRNG.TDLLDMQMHALLHQPHCGVPDGSDTSISPG  95
     .|...:|.|   .|::|: ::  .:::.|:||||..: |: |.
 51 NANSLEAKLKEMQKFFGLPITGMLNSHVIEIMQKPRCGVPDVAEYSLFPN 100

96 RCKWNKHTLTYRIINYPHDMKPSAVKDSIYNAVSIWSNVTPLIFQQVQNG 145
    ..||....:||||:.|.:|:.. .|.    : .|::|:. .|| |..| |
101 SPKWTSKVVTYRIVSYTRDLPHITVDRLVSKALNMWGKEIPLHFRKVVWG 150

146 DADIKVSFWQWAHEDGWPFDGPGGILGHAFLPNSGNPGVVHFDKNEHWS. 194
    .|||.::|  .  ||:|::|||||||..|:||| |..| .| .|||.:|:|.
151 TADIMIGFARGAHGDSYPFDGPGNTLAHAFAPGTGLGGDAHFDEDERWTD 200

195 ASDTGYNLFLVATHEIGHSLGLQHSGNQSSIMYPTYWYHDPRTFQLSADD 244
    :|. |.|:::..||||:|||||:.||::...:|||| ||..|.||.||
201 GSSLGINFLYAATHELGHSLGMGHSSDPNAVMYPTYGNGDPQNFKLSQDD 250

245 IQRIQHLYGEKCSS 258
    |. ||.|||.::.|
251 IKGIQKLYGKRSNS 264
```

FIG.5

HTEB072R (SEQ ID NO:7):

```
  1 AATTCGGCAC GAGGCGCTCT GGCTGAGCCA TGTTCCTTCT CCTCGCCCTC
 51 CTCACTGAGC TTGGAAGACT GCAAGCCCAC GAAGGTTCTG AAGGAATATT
101 TCTGCATGTC ACAGTTCCAC GGAAGATTAA GTCAAATGAC AGTGAAGTTT
151 CAGAGAGGAA GATGATTTAC ATCATTACAA TTGATGGACA ACCTTACACT
201 CTACATCTCG GAAAACAATC ATTCTTACCC CAGAACTTTT TGGTTTATAC
251 ATATAATGAA ACTGGATCTT TGCATTCTGT GTCTCCATAT TTTATGATGC
301 ATTGCCATTA CCAAGGGATA TGCTGCCGAA TNTTCCAANT TTCATTTGNG
351 ACACTCAGTA TATGGTNCTG GNCTCAGGTT AAAAAATCTT TTCAAAATTT
401 TTACCCCNAT ANTCTGGAAA TATACATTNT AGTGGGAAAG NTTNTGTATG
451 GTTANATGGG TCTGGAANTG ATGGNGTAAC ACAAANANTT NTCCNGGNTA
501 TTGGGT
```

HETAG43R (SEQ ID NO:9):

```
  1 GACAAATNAG GGTTTGGNAT GCAGCTCGTC ATCTTAAGAG TTACTATCTT
 51 CTTGCCCTGG TGTTTCGCCG TTCCAGTGCC CCCTGCTGCA GACCATAAAG
101 GATGGGACTT TGTTGAGGGC TATTTCCATC AATTTTTCCT GACCGAGAAG
151 GAGTCGCCAC TCCTTACCCA GGAGACACAA ACACAGCTCC TGCAACAATT
201 CCATCGGAAT GGGACAGACC TACTTGACAT GCAGT
```

HETAF71R (SEQ ID NO:8):

```
  1 AAATGAGGGT TTGGCATGCA GCTCGTCATC TTAAGAGTTA CTATCTTCTT
 51 GCCCTGGTGT TTCGCCGTTC CAGTGCCCCC TGCTGCAGAC CATAAAGGAT
101 GGGACTTTGT TGAGGGCTAT TTCCATCAAT TTTTCCTGAC CGAGAAGGAG
151 TCGCCACTCC TTACCCAGGA GACACAAACA CAGCTCCTGC AACAATTCCA
201 TCGGAATGGG ACAGACCTAC TTGACATGCA GATGCATGCT TCTGCTACAN
251 CAGCCCCACT GTGGGGTGCC TGATGGGTCC GACAACTNCA TCTCGCCAGG
301 AAGATGCAAG TGGATTAAGC ACA
```

FIG.7

```
  1 AGGAAATGAG GGTTTGGCAT GCAGCTCGTC ATCTTAAGAG TTACTATCTT CTTGCCCTGG
 61 TGTTTCGCCG TTCCAGTGCC CCCTGCTGCA GACCATAAAG GATGGGACTT TGTTGAGGGC
121 TATTTCCATC AATTTTTCCT GACCGAGAAG GAGTCGCCAC TCCTTACCCA GGAGACACAA
181 ACACAGCTCC TGCAACAATT CCATCGGAAT GGGACAGACC TACTTGACAT GCAGATGCAT
241 GCTCTGCTAC ACCAGCCCCA CTGTGGGGTG CCTGATGGGT CCGACAMCTC CATCTCGCCA
301 GGAAGATGCA AGTGGAATAA GCACACTCTA ACTTACAGGA TTATCAATTA CCCACATGAT
361 ATGAAGCCAT CCGCAGTGAA AGACAGTATA TATAATGCAG TTTCCATCTG GAGCAATGTG
421 ACCCCTTTGA TATTCCAGCA AGTGCAGAAT GGAGATGCAG ACATCAAGGT TTCTTTCTGG
481 CAGTGGGCCC ATGAAGATGG TTGSCCCTTT GATGGGCCAG GTGGTATCTT AGGCCATGCC
541 TTTTTACCAA ATTCTGGAAA TCCTGGAGTT GTCCATTTTG ACAAGAATGA ACACTGGTCA
601 GCTTCAGACA CTGGATATAA TCTGTTCCTG GTTGCAACTC ATGAGATTGG GCATTCTTTG
661 GGCCTGCAGC ACTCTGGGAA TCAGAGCTCC ATAATGTACC CCACTTACTG GTATCACGAC
721 CCTAGAACCT TCCAGCTCAG TGCCGATGAT ATCCAAAGGA TCCAGCATTT GTATGGAGAA
781 AAATGTTCAT CTGACATACC TTAATGTTAG CACAGAGGAC TTATTCAACC TGTCCTTTCA
841 GGGAGTTTAT TGGAGGATCA AAGAACTGAA AGCACTAGAG CAGCCTTGGG GACTGCTAGG
901 ATGAAGCCCT AAAGAATGCA ACCTAGTCAG GTTAGCTGAA CCGACACTCA AAACGCTACT
961 GAGTCACAAT AAAGATTGTT TTAAAGAGTA AAAAAAAAAA AAAAAAACTC GA
```

FIG.8

METALLOPROTEINASES

This application claims benefit of 35 U.S.C. section 119(e) based on copending U.S. Provisional Application Ser. Nos. 60/034,205, filed Jan. 21, 1997, 60/049,607, filed Jun. 13, 1997 and 60/054,541, filed Aug. 1, 1997.

BACKGROUND OF THE INVENTION

1. Field of the Invention

The present invention relates to novel metalloproteinases. More specifically, isolated nucleic acid molecules are provided encoding: (1) a human TNF-alpha converting enzyme ("TACE")-like protein, and (2) a matrilysin-like protein. TACE-like and matrilysin-like polypeptides are also provided, as are vectors, host cells, and recombinant methods for producing the same. The invention further relates to screening methods for identifying agonists and antagonists of the activity of these two enzymes. Also provided are diagnostic and therapeutic methods for detecting and treating diseases or disorders that involve these enzymes.

2. Related Art

Tumor necrosis factor-alpha (TNF-α) is a potent cytokine, secreted primarily by activated monocytes and macrophages, that contributes to a variety of inflammatory disease states and is broadly involved in immunomodulation. TNF-alpha is processed from an immature, membrane-bound form to a mature, secreted form by a metalloproteinase called TNF-alpha converting enzyme, or "TACE." See, R. A. Black et al., *Nature* 385:729–733 (February 1997); M. L. Moss et al., *Nature* 385:733–736 (February 1997); M. L. Moss et al., *J. Neuroimmunol.* 72:127–129 (Feb. 1997). Inhibitors of the enzyme TACE block secretion of TNF-alpha.

TACE is a new member of a protein family called "ADAMs" (proteins which contain A Disintegrin And Metalloprotease domain; also called adamalysins). See, Wolfsberg et al., *Dev. Biol.* 169:378–383 (1995).

The TACE/ADAM family is composed of membrane proteins with structural homology to the snake venom metalloproteases and disintegrins. Snake venom disintegrins are a family of anticoagulant peptides with a high cysteine content. A new member of TACE/ADAM in Drosophila, called the kuzbanian gene ("KUZ"), was found to be involved in Drosophila neurogenesis (Rooke, J. et al., *Science* 273:1227–1231 (August 1996)).

Approximately 11–13 ADAM genes have now been identified, including fertilin alpha and beta (involved in the integrin mediated binding and fusion of egg and sperm; previously known as PH-30 alpha and beta), epididymal apical protein I, cyritestin, MDC (a candidate for tumor suppressor in human breast cancer), meltrin- (mediates fusion of myoblast fusion in the process of myotube formation), MS2 (a macrophage surface antigen), and metargidin. Typical ADAMs are cell surface proteins which consist of pro-, metalloprotease-like, disintegrin-like, cysteine-rich, epidermal growth factor-like repeat, transmembrane and cytoplasmic domains.

A new ADAM family gene, named ADAMTS- 1, containing a disintegrin and metalloproteinase domain with thrombospondin (TSP) motifs, has now been shown to be closely associated with various inflammatory processes, as well as development of cancer cachexia. Kuno, K. et al., *J. Biol. Chem.* 272:556–562 (1997).

The disintegrin domain of ADAM family proteins functions in the prevention of integrin-mediated cell to cell and cell to matrix interactions, such as platelet aggregation, adhesion, and migration of tumor cells or neutrophils, and angiogenesis. Previously described disintegrins, such as contortrostatin (Trikha et al., *Cancer Research* 54:4993–4998 (1994) have been used to inhibit human metastatic melanoma (M24 cells) cell adhesion to type I collagen, vitronectin, and fibronectin, but not laminin. Further, contortrostatin inhibits lung colonization of M24 cells in a murine metastasis model.

The matrix metalloproteinases (MMPs) compose a family of structurally similar zinc-dependent enzymes that degrade all of the major components of the extracellular matrix. MMPs include the collagenases, gelatinases A and B, the stromelysins, matrilysin, metalloelastase, and the membrane-type matrix metalloproteinases. Over-expression and activation of MMPs have been linked with a range of diseases, such as arthritis, cancer, and multiple sclerosis. Regarding cancer, although MMPs classically have been implicated in basement membrane destruction associated with late-stage tumor cell invasion and metastasis, one MMP member, matrilysin, has recently been shown to be expressed in early stage human colorectal tumors. (C. L. Wilson et al., *Proc. Natl. Acad. Sci. USA* 94:1402–1407 (February 1997)).

Clearly, members of the TACE/ADAM family of proteins have a high potential for becoming valuable therapeutically and diagnostically. ADAM proteins, peptides derived from the sequence of ADAM proteins, and ADAM protein antagonists may become desirable components of molecular methods of assisting or preventing fertilization. Furthermore, specific TACE/ADAM proteins or derivatives may be useful in the detection and prevention of muscle disorders. TACE-like proteins also have an exciting potential in the treatment of inflammation, thrombosis, cancer, and cancer metastasis. TACE-like factors, or antagonists thereof, may also become useful agents in promoting macrophage or T-cell adhesion to matrices or cells' access to bound cytokines and other regulatory molecules.

Inhibitors of members of the matrix metalloproteinase (MMP) family (such as matrilysin) have been studied in the treatment or prophylaxis of cancer, cancer metastasis, as well as in the treatment of arthritis, corneal ulcers, pleural effusion, and multiple sclerosis. For a review on recent advances in matrix metalloproteinase research, see, Beckett, R. P. et al., *DDT* 1:16–26 (January 1996).

Clearly, there is a need in the art for novel TACE-like and matrilysin-like molecules, exhibiting sequence relatedness to known metalloproteinases with recognized therapeutic and diagnostic usefulness.

SUMMARY OF THE INVENTION

The present invention provides isolated nucleic acid molecules comprising a polynucleotide encoding the TACE-like polypeptide having the amino acid sequence shown in SEQ ID NO:2 or the amino acid sequence encoded by the cDNA clone deposited as ATCC Deposit Number 209042 on May 15, 1997. The present invention also provides isolated nucleic acid molecules comprising a polynucleotide encoding the matrilysin-like polypeptide having the amino acid sequence shown in SEQ ID NO: 5 or the amino acid sequence encoded by the cDNA clone deposited as ATCC Deposit Number 209055 on May 16, 1997.

The present invention also relates to recombinant vectors, which include the isolated nucleic acid molecules of the present invention, and to host cells containing the recombinant vectors, as well as to methods of making such vectors and host cells and for using them for production of TACE-like or matrilysin-like polypeptides or peptides by recombinant techniques.

The invention further provides isolated TACE-like or matrilysin-like polypeptides having an amino acid sequence encoded by a polynucleotide described herein.

The present invention also provides a screening method for identifying compounds capable of enhancing or inhibiting a cellular response induced by the TACE-like or matrilysin-like protein, which involves contacting cells which express the TACE-like or matrilysin-like protein with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

The invention provides a diagnostic method useful during diagnosis of cancer.

An additional aspect of the invention is related to a method for treating an individual in need of an increased level of TACE-like activity in the body comprising administering to such an individual a composition comprising a therapeutically effective amount of an isolated TACE-like polypeptide of the invention or an agonist thereof.

An additional aspect of the invention is related to a method for treating an individual in need of a decreased level of TACE-like activity in the body comprising administering to such an individual a composition comprising a therapeutically effective amount of a TACE-like polypeptide antagonist.

A still further aspect of the invention is related to a method for treating an individual in need of a decreased level of matrilysin-like activity in the body comprising, administering to such an individual a composition comprising a therapeutically effective amount of a matrilysin-like antagonist.

BRIEF DESCRIPTION OF THE FIGURES

FIG. 1 shows the nucleotide (SEQ ID NO:1) and deduced amino acid (SEQ ID NO:2) sequences of the TACE-like protein of the invention. The protein has a leader sequence of about 15 amino acid residues (first underlined portion) and a deduced molecular weight of about 20.9 kDa. It is further predicted that amino acid residues from about 169 to about 182 (second underlined portion) constitute the transmembrane domain.

FIG. 2 shows the regions of similarity between the amino acid sequences of the TACE-like polypeptide and tMDC II (SEQ ID NO:3).

FIGS. 4a and 4b show the nucleotide (SEQ ID NO:4) and deduced amino acid (SEQ ID NO:5) sequences of the matrilysin-like protein of the invention. The protein has a leader sequence of about 22 amino acid residues (underlined) and a deduced molecular weight of about 29.7 kDa.

FIG. 5 shows the regions of similarity between the amino acid sequences of the matrilysin-like protein and human matrilysin (SEQ ID NO:6).

FIG. 7 shows sequence HTEBO72R (SEQ ID NO: 7); HETAG43R (SEQ ID NO: 9) and HETAF71R (SEQ ID NO: 8).

FIG. 8 shows the nucleotide sequence (SEQ ID NO:20) derived from HETAF71 as it appeared in U.S. Provisional Patent Application Ser. Nos. 60/049,607.

DETAILED DESCRIPTION OF THE PREFERRED EMBODIMENTS

Figure 3:
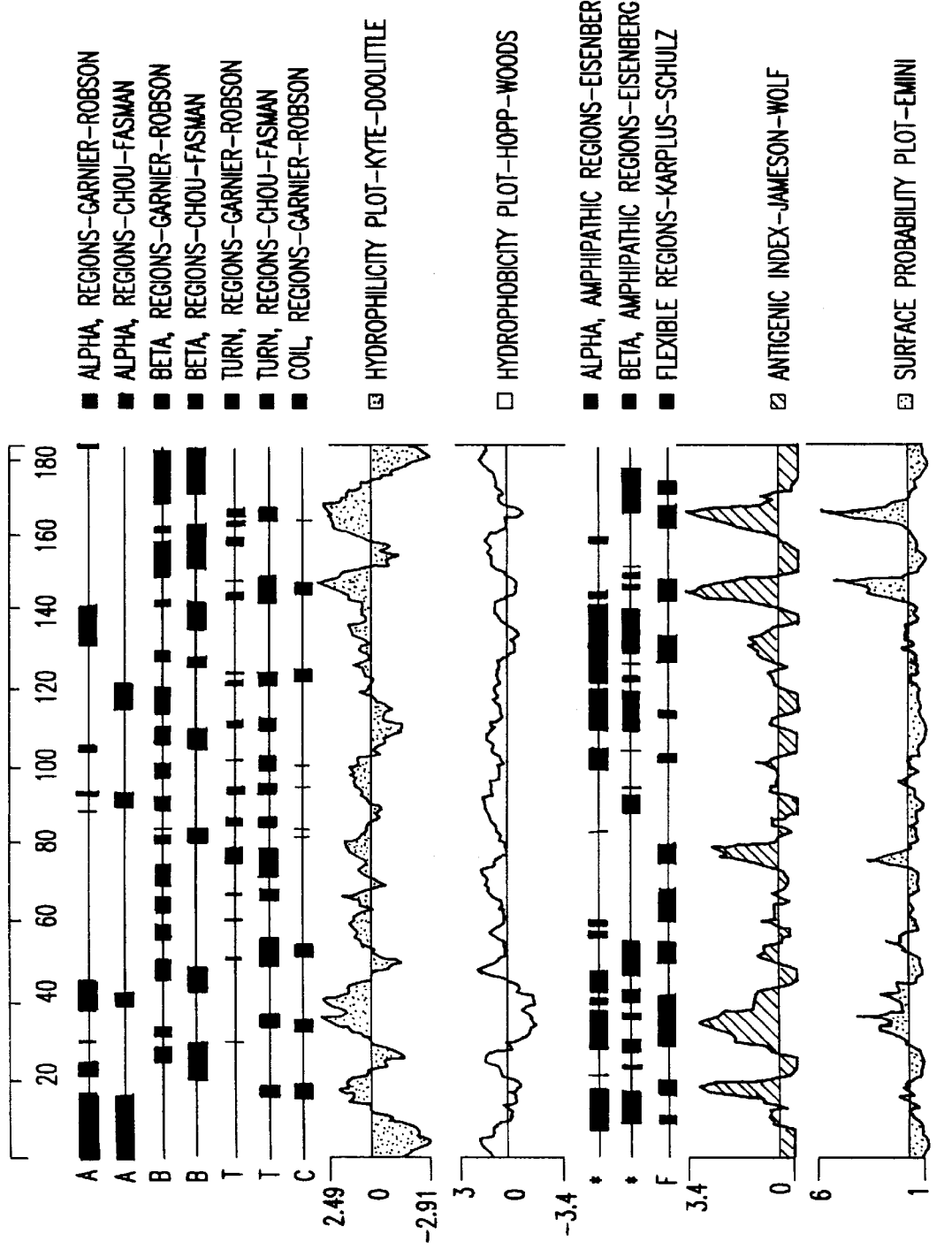
FIG. 3 shows an analysis of the TACE-like amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 13 to about 22, about 31 to about 46, 55 to about 103, 123 to about 151, and 159 to about 173 in FIG. 1 correspond to the shown highly antigenic regions of the TACE-like protein.
Figure 6:
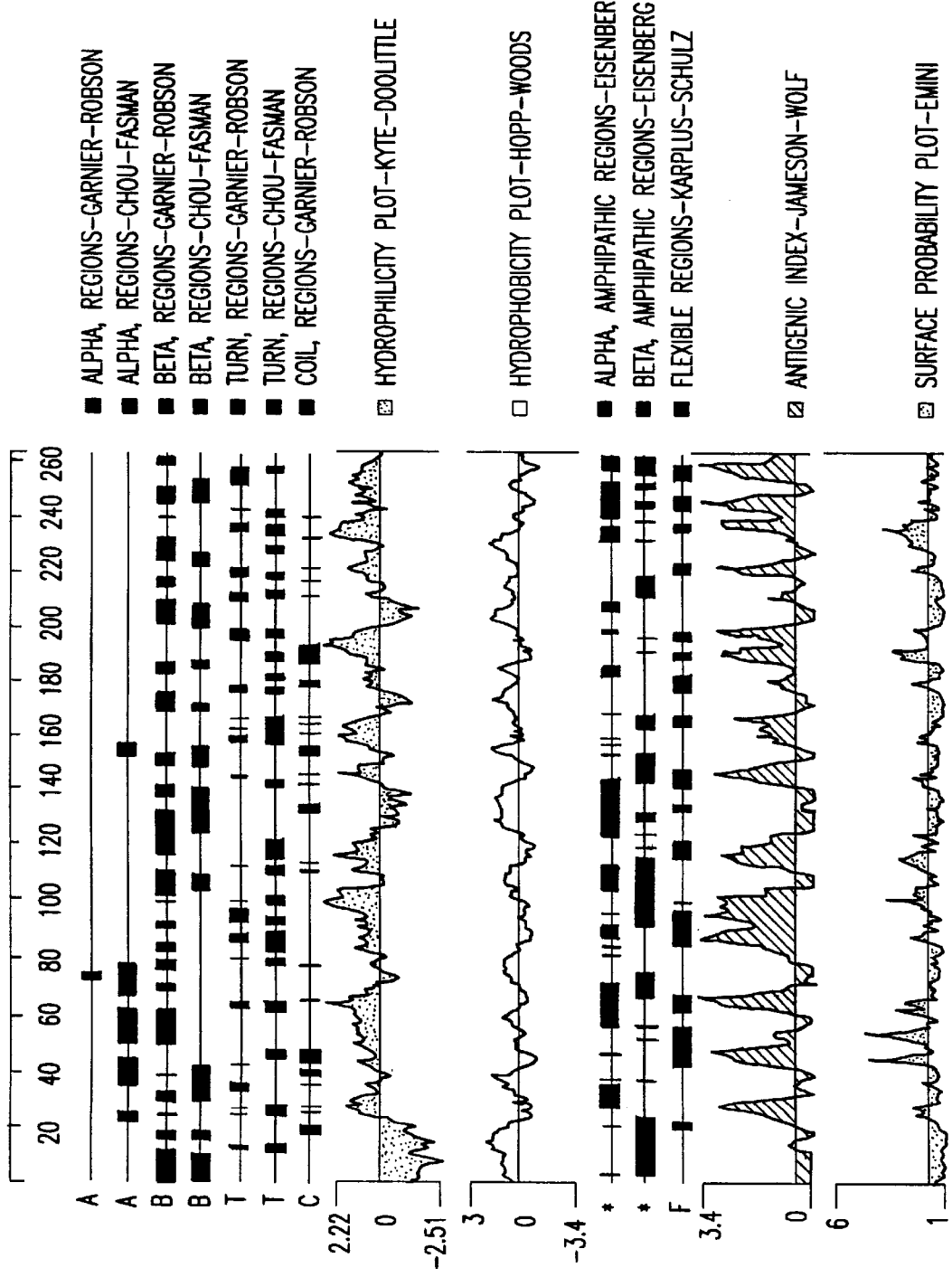
FIG. 6 shows an analysis of the matrilysin-like amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 24 to about 71, about 81 to about 125, 141 to about 167, 178 to about 202, and 212 to about 260 in FIG. 1 correspond to the shown highly antigenic regions of the matrilysin-like protein.

The present invention provides isolated nucleic acid molecules comprising a polynucleotide encoding a TACE-like or matrilysin-like polypeptide having the amino acid sequence shown in SEQ ID NO:2 or SEQ ID NO:5, respectively, which was determined by sequencing cloned cDNA.

The TACE-like protein of the present invention shares sequence homology with tMDC II (FIG. 2) (SEQ ID NO:3). The nucleotide sequence shown in SEQ ID NO:1 was obtained by sequencing a cDNA clone ("HTEJQ70"), which was deposited on May 15, 1997 at the American Type Culture Collection, 12301 Park Lawn Drive, Rockville, Md. 20852, and given accession number 209042. The deposited clone is inserted in the pBluescript SK(-) plasmid (Stratagene, LaJolla, Calif.).

The matrilysin-like protein of the present invention shares sequence homology with human matrilysin (FIG. 2) (SEQ ID NO:6). The nucleotide sequence shown in SEQ ID NO:4 was obtained by sequencing a cDNA clone ("HETBW05"), which was deposited on May 16, 1997 at the American Type Culture Collection, 12301 Park Lawn Drive, Rockville, Md. 20852, and given accession number 209055. The deposited clone is inserted in the pBluescript SK(-) plasmid (Stratagene, LaJolla, Calif.). A related clone has also been discovered the polynucleotide sequence of which is shown in FIG. 8. This clone, HETAF71, was also deposited with the ATCC, along with other cDNA clones as a mixture, on Jun. 5, 1997 and given accession number 209090. These clones are belived to be derived from the same gene and are further believed to encode the same polypeptide. Discrepancies between the sequence shown in FIG. 4 (SEQ ID NO:4) and the sequence shown in FIG. 8 (SEQ ID NO:20) are believed to be due to errors in the DNA sequencing process, as is described below. In case of conflict, such discrepancies should be resolved in favor of SEQ ID NO:4 and clone HETBW05. The remaining description of the invention as it pertains to matrilysin-like protein references HETBW05 (SEQ ID NO:4) and the polypeptide encoded thereby, however, it is the intention of the applicants that HETAF71 (SEQ ID NO:8) and the protein encoded thereby could equally be substituted in place of HETBW05. Accordingly, it will be appreciated that applicants intend to encompass HETAF71 within the invention in all respects as it pertains to HETBW05.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO: 1 or SEQ ID NO:4, a nucleic acid molecule of the present invention encoding a TACE-like or matrilysin-like polypeptide may be obtained using standard cloning and screening procedures, such as those for cloning cDNAs using mRNA as starting material.

Illustrative of the invention, the nucleic acid molecule described in SEQ ID NO:1 was discovered in a cDNA library derived from human testes. The gene was also identified in cDNA libraries from amniotic cells (primary culture) and keratinocytes The determined nucleotide sequence of the TACE-like cDNA of SEQ ID NO:1 contains an open reading frame encoding a protein of about 182 amino acid residues, a predicted leader sequence of about 15 amino acid residues, and a deduced molecular weight of about 20.9 kDa. The TACE-like protein shown in SEQ ID NO:2 is about 44% identical and about 62% similar to tMDC II (FIG. 2).

Also illustrative of the invention, the nucleic acid molecule described in SEQ ID NO:4 was discovered in a cDNA library derived from human umbilical vein endothelial cells. The gene was also identified in cDNA libraries from the following tissues: primarily human endometrial tumor; but also in human colon, CD34+ cells, human B-cell lymphoma, and endothelial induced human microvascular endothelial cells. The determined nucleotide sequence of the matrilysin-like cDNA of SEQ ID NO:4 contains an open reading frame encoding a protein of about 261 amino acid residues, a predicted leader sequence of about 22 amino acid residues, and a deduced molecular weight of about 29.7 kDa. The matrilysin-like protein shown in SEQ ID NO:5 is about 39% identical and about 59% similar to human matrilysin (FIG. 5).

The present invention also provides the mature form(s) of the TACE-like and matrilysin-like proteins of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature TACE-like polypeptide having the amino acid sequence encoded by the cDNA clone contained in the host identified as ATCC Deposit No. 209042 and as shown in SEQ ID NO:2. By the mature TACE-like protein having the amino acid sequence encoded by the cDNA clone contained in the host identified as ATCC Deposit 209042 is meant the mature form(s) of the TACE-like protein produced by expression in a mammalian cell (e.g., COS cells, as described below) of the complete open reading frame encoded by the human DNA sequence of the clone contained in the vector in the deposited host. As indicated below, the mature TACE-like protein having the amino acid sequence encoded by the cDNA clone contained in ATCC Deposit No. 209042 may or may not differ from the predicted "mature" TACE-like protein shown in SEQ ID NO:2 (amino acids from about 16 to about 182) depending on the accuracy of the predicted cleavage site based on computer analysis.

The present invention also provides a nucleotide sequence encoding the mature matrilysin-like polypeptide having the amino acid sequence encoded by the cDNA clone contained in the host identified as ATCC Deposit No. 209055 and as shown in SEQ ID NO:5. By the mature matrilysin-like protein having the amino acid sequence encoded by the cDNA clone contained in the host identified as ATCC Deposit 209055 is meant the mature form(s) of the matrilysin-like protein produced by expression in a mammalian cell (e.g., COS cells, as described below) of the complete open reading frame encoded by the human DNA sequence of the clone contained in the vector in the deposited host. As indicated below, the mature matrilysin-like protein having the amino acid sequence encoded by the cDNA clone contained in ATCC Deposit No. 209055 may or may not differ from the predicted "mature" matrilysin-like protein shown in SEQ ID NO:5 (amino acids from about 23 to about 261) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete TACE-like and matrilysin-like polypeptides of the present invention were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NOS:2 and 5. Thereafter, the complete amino acid sequences were further analyzed by visual inspection, applying a simple form of the (−1,−3) rule of von Heinje. von Heinje, supra.

Thus, the leader sequence for the TACE-like protein is predicted to consist of amino acid residues from about 1 to about 15 in SEQ ID NO:2, while the mature TACE-like protein is predicted to consist of residues from about 16 to about 182.

As one of ordinary skill would appreciate, due to the possibilities of sequencing errors, as well as the variability of cleavage sites for leaders in different known proteins, the predicted TACE-like polypeptide encoded by the deposited cDNA comprises about 182 amino acids, but may be anywhere in the range of about 172 to about 192 amino acids; and the predicted leader sequence of this protein is about 15 amino acids, but may be anywhere in the range of about 5 to about 25 amino acids.

The leader sequence for the matrilysin-like protein is predicted to consist of amino acid residues from about −1 to about 22in SEQ ID NO:2, while the mature matrilysin-like protein is predicted to consist of residues from about 23 to about 261.

As one of ordinary skill would appreciate, due to the possibilities of sequencing errors, as well as the variability of cleavage sites for leaders in different known proteins, the predicted matrilysin-like polypeptide encoded by the deposited cDNA comprises about 261 amino acids, but may be anywhere in the range of about 251 to about 271 amino acids; and the predicted leader sequence of this protein is about 22 amino acids, but may be anywhere in the range of about 12 to about 32 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1 or SEQ ID NO:4; DNA molecules comprising the coding sequence for the mature TACE-like or matrilysin-like protein; and DNA molecules which comprise a sequence substantially different from those described above but which, due to the degeneracy of the genetic code, still encode the TACE-like or matrilysin-like protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1 which have been determined from the following related cDNA clone: HTEBO72R (SEQ ID NO:7).

In addition, the invention provides nucleic acid molecules having nucleotide sequences related to extensive portions of SEQ ID NO:4, which have been determined from the following related cDNA clones: HETAF71R (SEQ ID NO:8) and HETAG43R (SEQ ID NO:9).

In another aspect, the invention provides isolated nucleic acid molecules encoding the TACE-like polypeptide having an amino acid sequence as encoded by the cDNA clone contained in the plasmid deposited as ATCC Deposit No. 209042 on May 15, 1997. In a further embodiment, nucleic acid molecules are provided encoding the mature TACE-like polypeptide or the full-length TACE-like polypeptide lacking the N-terminal methionine. The invention also provides an isolated nucleic acid molecule having the nucleotide sequence shown in SEQ ID NO:1 or the nucleotide sequence of the TACE-like cDNA contained in the above-described deposited clone, or a nucleic acid molecule having a sequence complementary to one of the above sequences.

The invention also provides isolated nucleic acid molecules encoding the matrilysin-like polypeptide having an amino acid sequence as encoded by the cDNA clone contained in the plasmid deposited as ATCC Deposit No. 209055 on May 16, 1997. In a further embodiment, nucleic acid molecules are provided encoding the mature matrilysin-like polypeptide or the full-length matrilysin-like polypeptide lacking the N-terminal methionine. The invention also provides an isolated nucleic acid molecule having the nucleotide sequence shown in SEQ ID NO:4 or the nucleotide sequence of the matrilysin-like cDNA contained in the above-described deposited clone, or a nucleic acid molecule having a sequence complementary to one of the above sequences.

Such isolated molecules, discussed supra, particularly DNA molecules, are useful as probes for gene mapping, by in situ hybridization with chromosomes, and for detecting expression of the TACE-like or matrilysin-like gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NOS:1 or 4 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length (TACE-like) and 50–700 nt in length (matrilysin-like) are also useful according to the present invention as are fragments corresponding to most, if not all, of the nucleotide sequence of the deposited cDNA or as shown in SEQ ID NOS:1 or 4. By a fragment at least 20 nt in length, for example, is intended fragments, which include 20 or more contiguous bases from the nucleotide sequence of the deposited cDNA or the nucleotide sequence as shown in SEQ ID NOS:1 or 4.

Preferred nucleic acid fragments of the present invention include nucleic acid molecules encoding: a polypeptide comprising the TACE-like transmembrane domain (predicted to constitute amino acid residues from about 169 to about 182 in SEQ ID NO:2) As above with the leader sequence, the amino acid residues constituting the TACE-like transmembrane domain has been predicted by computer analysis. Thus, as one of ordinary skill would appreciate, the amino acid residues constituting this domains may vary slightly (e.g., by about 1 to about 15 amino acid residues) depending on the criteria used to define each domain.

Preferred nucleic acid fragments of the present invention also include nucleic acid molecules encoding epitope-bearing portions of the TACE-like protein. In particular, such nucleic acid fragments of the present invention include nucleic acid molecules encoding: a polypeptide comprising amino acid residues from about 13 to about 22 in SEQ ID NO:2; a polypeptide comprising amino acid residues from about 31 to about 46 in SEQ ID NO:2; a polypeptide comprising amino acid residues from about 55 to about 103 in SEQ ID NO:2; a polypeptide comprising amino acid residues from about 123 to about 151 in SEQ ID NO:2; and a polypeptide comprising amino acid residues from about 159 to about 173 in SEQ ID NO:2. The inventors have determined that the above polypeptide fragments are antigenic regions of the TACE-like protein. Methods for determining other such epitope-bearing portions of the TACE-like protein are described in detail below.

Other preferred nucleic acid fragments of the present invention include nucleic acid molecules encoding epitope-bearing portions of the matrilysin-like protein. In particular, such nucleic acid fragments of the present invention include nucleic acid molecules encoding: a polypeptide comprising amino acid residues from about 24 to about 71 in SEQ ID NO:5; a polypeptide comprising amino acid residues from about 81 to about 125 in SEQ ID NO:5; a polypeptide comprising amino acid residues from about 141 to about 167 in SEQ ID NO:5; a polypeptide comprising amino acid residues from about 173 to about 202 in SEQ ID NO:5; and a polypeptide comprising amino acid residues from about 212 to about 260 in SEQ ID NO:5. The inventors have determined that the above polypeptide fragments are antigenic regions of the matrilysin-like protein. Methods for determining other such epitope-bearing portions of the matrilysin- like protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 209042 or ATCC Deposit 209055. By "stringent hybridization conditions" is intended overnight incubation at 42 C. in a solution comprising: 50% formamide, 5×SSC (750 mM NaCl, 75 m trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65 C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1 or SEQ ID NO:4). Of course, a polynucleotide which hybridizes only to a poly A sequence (such as the 3 terminal poly(A) tract of the TACE-like cDNA shown in SEQ ID NO:1 or the matrilysin-like cDNA shown in SEQ ID NO:4), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone). Particularly preferred regions for selecting such fragments include the coding regions shown in FIGS. 1 and 4; i.e., nucleotides 22 through 567 of SEQ ID NO:1 and nucleotides 46 through 827 of SEQ ID NO:4.

As indicated, nucleic acid molecules of the present invention which encode a TACE-like or matrilysin-like polypeptide may include, but are not limited to those encoding the amino acid sequence of the mature polypeptide, by itself; the coding sequence for the mature polypeptide and additional sequences, such as those encoding the leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5 and 3 sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the TACE-like or matrilysin-like protein fused to Fc at the N- or C-terminus.

The present invention further relates to variants of the nucleic acid molecules of the present invention, which encode portions, analogs or derivatives of the TACE-like or matrilysin-like protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TACE-like or matrilysin-like protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 16 to about 182 in SEQ ID NO:2; (d) a nucleotide sequence encoding the polypeptide having the amino acid sequence encoded by the cDNA clone contained in ATCC Deposit No. 209042; (e) a nucleotide sequence encoding the mature TACE-like polypeptide having the amino acid sequence encoded by the cDNA clone contained in ATCC Deposit No. 209042; (f) a nucleotide sequence encoding the TACE-like transmembrane domain; or (g) a nucleotide sequence complementary to any of the nucleotide sequences in (a), (b), (c), (d), (e), or (f).

Additional embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the polypeptide having the amino acid sequence in SEQ ID NO:5; (b) a nucleotide sequence encoding the polypeptide having the amino acid sequence in SEQ ID NO:5, but lacking the N-terminal methionine; (c) a nucleotide sequence encoding the polypeptide having the amino acid sequence at positions from about 23 to about 261 in SEQ ID NO:5; (d) a nucleotide sequence encoding the polypeptide having the amino acid sequence encoded by the cDNA clone contained in ATCC Deposit No. 209055; (e) a nucleotide sequence encoding the mature matrilysin-like polypeptide having the amino acid sequence encoded by the cDNA clone contained in ATCC Deposit No. 209055; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a TACE-like or matrilysin-like polypeptide is intended that the nucleotide sequence of the polynucleotide is identical to the reference sequence except that the polynucleotide sequence may include up to five point mutations per each 100 nucleotides of the reference nucleotide sequence encoding the TACE-like or matrilysin-like polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in SEQ ID NO:1 or SEQ ID NO:4, or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in SEQ ID NO:1 or SEQ ID NO:4, or to the nucleic acid sequence of the deposited cDNA, irrespective of whether they encode a polypeptide having TACE-like or matrilysin-like activity. This is because even where a particular nucleic acid molecule does not encode a polypeptide having TACE-like or matrilysin-like activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TACE-like or matrilysin-like activity include, inter alia, (1) isolating the TACE-like or matrilysin-like gene or allelic variants thereof in a cDNA library; (2) in situ hybridization (e.g., "FISH") to metaphase chromosomal spreads to provide precise chromosomal location of the TACE-like or matrilysin-like genes, as described in Verma et al., *Human Chromosomes: A Manual of Basic Techniques*, Pergamon Press, New York (1988); and Northern Blot analysis for detecting TACE-like or matrilysin-like mRNA expression in specific tissues.

Preferred, however, are nucleic acid molecules having sequences at least 90%, 95%, 96%, 97%, 98% or 99% identical to a nucleic acid sequence shown in SEQ ID NO:1 or SEQ ID NO:4, or to a nucleic acid sequence of the deposited cDNA which do, in fact, encode a polypeptide having TACE-like or matrilysin-like protein activity. By "a polypeptide having TACE-like activity" is intended polypeptides exhibiting TACE-like activity in a particular biological assay. For example, TACE-like protein activity can be measured using an assay for in vitro TNF-alpha precursor cleavage, as described in Robache-Gallea, S. et al. *J. Biol. Chem.* 270:23688–23692 (October 1995). By "a polypeptide having matrilysin-like activity" is intended polypeptides exhibiting matrilysin-like activity in a particular biological assay. For example, matrilysin-like protein activity can be measured using the assays described in C. L. Wilson et al., *Int. J. Biochem. Cell. Biol.* 28:123–136 (1996) or C. L. Wilson et al., *Proc. Natl. Acad. Sci. USA* 94:1402–1407 (February 1997).

Of course, due to the degeneracy of the genetic code, one of ordinary skill in the art will immediately recognize that a large number of the nucleic acid molecules having a sequence at least 90%, 95%, 96%, 97%, 98%, or 99% identical to a nucleic acid sequence of the deposited cDNA or a nucleic acid sequence shown in SEQ ID NO:1 or SEQ ID NO:4 will encode a polypeptide "having TACE-like or matrilysin-like protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TACE-like or matrilysin-like protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science*

247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of TACE-like and matrilysin-like polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as an antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:9459–9471 (1995).

The TACE-like or matrilysin-like protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

TACE-Like and Matrilysin-Like Polypeptides and Fragments

The invention further provides an isolated TACE-like or matrilysin-like polypeptide having the amino acid sequence encoded by the deposited cDNAs, or the amino acid sequence in SEQ ID NO:2 or SEQ ID NO:5, or a peptide or polypeptide comprising a portion of the above polypeptides.

It will be recognized in the art that some amino acid sequences of the TACE-like or matrilysin-like polypeptide can be varied without significant effect on the structure or function of the protein. If such differences in sequence are to contemplated, it should be remembered that there will be critical areas on the protein which determine activity.

Thus, the invention further includes variations of the TACE-like or matrilysin-like polypeptide which show substantial TACE-like or matrilysin-like polypeptide activity or which include regions of TACE-like or matrilysin-like protein such as the protein portions discussed below. Such mutants include deletions, insertions, inversions, repeats, and type substitutions. As indicated above, guidance concerning which amino acid changes are likely to be phenotypically silent can be found in J. U. Bowie et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:5, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TACE-like or matrilysin-like protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF- to only one of the two known types of TNF receptors. Thus, the metalloproteinases of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TACE-like and matrilysin-like protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)). The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TACE-like or matrilysin-like polypeptide can be substantially purified by the one-step method described in Smith and Johnson, *Gene* 67:31–40 (1988).

The TACE-like polypeptides of the present invention include the polypeptide encoded by the deposited cDNA including the leader; the mature polypeptide encoded by the deposited the cDNA minus the leader (i.e., the mature protein); a polypeptide comprising amino acids about 1 to about 182 in SEQ ID NO:2; a polypeptide comprising amino acids about 2 to about 182 in SEQ ID NO:2; a polypeptide comprising amino acids about 16 to about 182 in SEQ ID NO:2; a polypeptide comprising the transmembrane domain; as well as polypeptides which are at least 80% identical, more preferably at least 90% or 95% identical, still more preferably at least 96%, 97%, 98% or 99% identical to those described above and also include portions of such polypeptides with at least 30 amino acids and more preferably at least 50 amino acids.

The matrilysin-like polypeptides of the present invention include the polypeptide encoded by the deposited cDNA including the leader; the mature polypeptide encoded by the deposited the cDNA minus the leader (i.e., the mature protein); a polypeptide comprising amino acids about 1 to about 261 in SEQ ID NO:5; a polypeptide comprising amino acids about 2 to about 261 in SEQ ID NO:5; a polypeptide comprising amino acids about 23 to about 261 in SEQ ID NO:5; as well as polypeptides which are at least 80% identical, more preferably at least 90% or 95% identical, still more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a TACE-like or matrilysin-like polypeptide is intended that the amino acid sequence of the polypeptide is identical to the reference sequence except that the polypeptide sequence may include up to five amino acid alterations per each 100 amino acids of the reference amino acid of the TACE-like or matrilysin-like polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or SEQ ID NO:5, or to the amino acid sequence encoded by the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention are useful as molecular weight markers on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate TACE-like-specific antibodies include: a polypeptide comprising amino acid residues from about 13 to about 22 in SEQ ID NO:2; a polypeptide comprising amino acid residues from about 31 to about 46 in SEQ ID NO:2; a polypeptide comprising amino acid residues from about to about 88 in SEQ ID NO:2; a polypeptide comprising amino acid residues from about 123 to about 151 in SEQ ID NO:2; and a polypeptide comprising amino acid residues from about 159 to about 173 in SEQ ID NO 2. As indicated above, the inventors have determined that the above polypeptide fragments are antigenic regions of the TACE-like protein.

Non-limiting examples of antigenic polypeptides or peptides that can be used to generate matrilysin-like-specific antibodies include: a polypeptide comprising amino acid residues from about 24 to about 71 in SEQ ID NO:5; a polypeptide comprising amino acid residues from about 81 to about 125 in SEQ ID NO:5; a polypeptide comprising amino acid residues from about 141 to about 167 in SEQ ID NO:5; a polypeptide comprising amino acid residues from about 173 to about 202 in SEQ ID NO:5; and a polypeptide comprising amino acid residues from about 212 to about 260 in SEQ ID NO:5. As indicated above, the inventors have determined that the above polypeptide fragments are antigenic regions of the matrilysin-like protein.

The epitope-bearing peptides and polypeptides of the invention may be produced by any conventional means. Houghten, R. A., "General Method for the Rapid Solid-Phase Synthesis of Large Numbers of Peptides: Specificity of Antigen-Antibody Interaction at the Level of Individual Amino Acids, *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, TACE-like or matrilysin-like polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TACE-like or matrilysin-like protein or protein fragment alone (Fountoulakis et al., *J. Biochem* 270:3958–3964 (1995)).

Matrilysin-like Protein in Cancer Diagnosis and Prognosis

The expression of matrix metalloproteinases (MMPs) in neoplastic lesions has been well-documented. The mRNA of one MMP, matrilysin ("MMP-7"), has been detected in human adenomas, as well as carcinomas and adenocarcinomas of the breast and colon. Heppner, K. J. et al., *Am. J. Pathol.* 149:273–282 (1996); Wolf, C. et al., *Proc. Natl. Acad. Sci. USA* 90:1843–1847 (1993). MMP-7 has also been reported to be expressed in human gastric carcinomas. Honda, M. et al., *Gut* 39:444–448 (1996). Recently, Wilson, C. L. et al., *Proc. Natl. Acad. Sci. USA* 94:1402–1407 (February 1997), has reported that matrilysin is expressed in a high percentage of early-stage human colorectal tumors. Accordingly, it is believed that certain tissues in mammals with cancer express significantly enhanced levels of the matrilysin-like protein and mRNA encoding the matrilysin-like protein when compared to a corresponding "standard" mammal, i.e., a mammal of the same species not having the cancer. Further, it is believed that enhanced levels of the matrilysin-like protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the matrilysin-like protein in mammalian cells or body fluid and comparing the gene expression level with a standard matrilysin-like gene expression level, whereby an increase in the gene expression level over the standard is indicative of certain tumors.

Where a tumor diagnosis has already been made according to conventional methods, the present invention is useful as a prognostic indicator, whereby patients exhibiting enhanced matrilysin-like gene expression will experience a worse clinical outcome relative to patients expressing the gene at a lower level.

By "assaying the expression level of the gene encoding the matrilysin-like protein" is intended qualitatively or quantitatively measuring or estimating the level of the matrilysin-like protein or the level of the mRNA encoding the matrilysin-like protein in a first biological sample either directly (e.g., by determining or estimating absolute protein level or mRNA level) or relatively (e.g., by comparing to the matrilysin-like protein level or mRNA level in a second biological sample).

Preferably, the matrilysin-like protein level or mRNA level in the first biological sample is measured or estimated and compared to a standard matrilysin-like protein level or mRNA level, the standard being taken from a second biological sample obtained from an individual not having the cancer. As will be appreciated in the art, once a standard matrilysin-like protein level or mRNA level is known, it can be used repeatedly as a standard for comparison.

By "biological sample" is intended any biological sample obtained from an individual, cell line, tissue culture, or other source which contains matrilysin- like protein or mRNA. Biological samples include mammalian body fluids (such as sera, plasma, urine, synovial fluid and spinal fluid) which contain secreted mature matrilysin-like protein, and ovarian, prostate, heart, placenta, pancreas liver, spleen, lung, breast and umbilical tissue.

The present invention is useful for detecting cancer in mammals. In particular the invention is useful during diagnosis of the following types of cancers in mammals: intestinal (colon), stomach, breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal. Biochem.* 162:156–159 (1987). Levels of mRNA encoding the matrilysin-like protein are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxaldimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Matrilysin-like protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the matrilysin-like protein). Northern blot analysis can be performed as described above.

Preferably, levels of mRNA encoding the matrilysin-like protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the matrilysin-like protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying matrilysin-like protein levels in a biological sample can occur using any art-known method. Preferred for assaying matrilysin-like protein levels in a biological sample are antibody-based techniques. For example, matrilysin-like protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of matrilysin-like protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of matrilysin-like protein can be accomplished using isolated matrilysin-like protein as a standard. This technique can also be applied to body fluids. With these samples, a molar concentration of matrilysin-like protein will aid to set standard values of matrilysin-like protein content for different body fluids, like serum, plasma, urine, spinal fluid, etc. The normal appearance of matrilysin-like protein amounts can then be set using values from healthy individuals, which can be compared to those obtained from a test subject.

Other antibody-based methods useful for detecting matrilysin-like protein gene expression include immunoassays, such as the enzyme linked immunosorbent assay (ELISA) and the radioimmunoassay (RIA). For example, a matrilysin-like protein-specific monoclonal antibodies can be used both as an immunoabsorbent and as an enzyme-labeled probe to detect and quantify the matrilysin-like protein. The amount of matrilysin-like protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect matrilysin-like protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting matrilysin-like protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

In addition to assaying matrilysin-like protein levels in a biological sample obtained from an individual, matrilysin-like protein can also be detected in vivo by imaging. Antibody labels or markers for in vivo imaging of matrilysin-like protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A matrilysin-like protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain matrilysin-like protein. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Matrilysin-like-protein specific antibodies for use in the present invention can be raised against the intact matrilysin-like protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) that are capable of specifically binding to matrilysin-like protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the matrilysin-like protein or an antigenic fragment thereof can be administered to an animal in order to induce the production of sera containing polyclonal antibodies. In a preferred method, a preparation of matrilysin-like protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or matrilysin-like protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a matrilysin-like protein antigen or, more preferably, with a matrilysin-like protein-expressing cell. Suitable cells can be recognized by their capacity to bind anti-matrilysin-like protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the matrilysin-like protein antigen.

Alternatively, additional antibodies capable of binding to the matrilysin- like protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method,matrilysin-like-protein specific antibodies are used to immunize an animal, preferably a mouse. The splenocytes of such an animal are then used to produce hybridoma cells, and the hybridoma cells are screened to identify clones which produce an antibody whose ability to bind to the matrilysin-like protein-specific antibody can be blocked by the matrilysin-like protein antigen. Such antibodies comprise anti-idiotypic antibodies to the matrilysin-like protein-specific antibody and can be used to immunize an animal to induce formation of further matrilysin-like protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, matrilysin-like protein-binding fragments can be produced through the application of recombinant DNA technology or through synthetic chemistry.

Where in vivo imaging is used to detect enhanced levels of matrilysin-like protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the matrilysin-like protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I- labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J. Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Screening for Antagonists and Agonists

The present invention also provides a method of screening compounds to identify those which enhance or block the action of the TACE-like or matrilysin-like protein on cells, such as its interaction with molecules that bind TACE-like or matrilysin-like proteins. An agonist is a compound which increases the natural biological functions of TACE-like or matrilysin-like protein, or which functions in a manner similar to TACE-like or matrilysin-like protein, while antagonists decrease or eliminate such functions. For example, a cellular compartment such as a membrane or a preparation thereof may be prepared from a cell that expresses a molecule that binds TACE-like or matrilysin-like proteins. The preparation is then incubated with labeled TACE-like or matrilysin-like protein in the absence of or presence of a candidate compound which may be a TACE-like or matrilysin-like antagonist or agonist. The ability of the candidate compound to bind the binding molecule is reflected in decreased binding of the labeled ligand. Compounds which bind gratuitously (i.e., without inducing the effects of TACE-like or matrilysin-like proteins on binding the TACE-like or matrilysin-like binding molecule) are most likely good antagonists. Compounds that bind well and elicit effect that are the same as or closely related to TACE-like or matrilysin-like proteins are agonists.

In another aspect, a screening assay for agonists and antagonists is provided which involves determining the effect a candidate compound has on TACE-like binding to the TNF-alpha precursor. In particular, the method involves contacting the TNF-alpha precursor with a TACE-like polypeptide and a candidate compound and determining whether TACE-like polypeptide binding to the TNF-alpha precursor is increased or decreased due to the presence of the candidate compound.

Potential antagonists include small organic molecules, peptides, polypeptides, and antibodies that bind to a polypeptide of the invention and thereby inhibitits activity. Potential antagonists also include antisense molecules For a review, see, Okano, J., *J. Neurochem.* 56:560 (1991).

Agonists of the TACE-like protein of the invention may be used to enhance the action of TACE-like proteins, for example, in the treatment of cancer, or any disease characterized by an underproduction of TNF-alpha. Antagonists of the TACE-like protein of the invention may be used to inhibit the action of TACE-like proteins, for example, in the treatment of disorders characterized by an overproduction of TNF-alpha, such as inflammation, immune system disorders, infectious disease, or neurological disease.

Antagonists of the matrilysin-like protein of the invention may be used to inhibit the action of the matrilysin-like protein of the invention, for example, in the treatment or prophylaxis of disorders characterized by degradation of the extracellular matrix, such as, for example, cancer, arthritis, cardiovascular disorders, cachexia, and multiple sclerosis.

The agonists and antagonists described herein may be employed in a composition with a pharmaceutically acceptable carrier, as described below.

Therapeutics

As discussed above, the TACE-like protein of the invention or agonists thereof may be used in the treatment of cancer, or any disease characterized by an underproduction of TNF-alpha. Antagonists of the TACE-like protein of the invention may be used to inhibit the action of TACE-like proteins, for example, in the treatment of disorders characterized by an overproduction of TNF-alpha, such as inflammation, immune system disorders, infectious disease, or neurological disease.

Matrix metalloproteinase (MMP) inhibitors, such as an antagonist of the matrilysin-like protein of the invention, may be used to inhibit the action of matrilysin-like proteins, for example, in the treatment of disorders characterized by degradation of the extracellular matrix, such as, e.g, cancer, arthritis, cardiovascular disorders, cachexia, immune system disorders, digestive disorders and multiple sclerosis.

Modes of Administration

It will be appreciated that conditions caused by a decrease in the standard or normal level of TACE-like activity in an individual, can be treated by administration of the TACE-like protein. Thus, the invention further provides a method of treating an individual in need of an increased level of TACE-like activity comprising administering to such an individual a pharmaceutical composition comprising an effective amount of an isolated TACE-like polypeptide of the invention, particularly a mature form of the TACE-like protein, effective to increase the TACE-like activity level in such an individual.

As a general proposition, the total pharmaceutically effective amount of TACE-like polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TACE-like polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed.

Pharmaceutical compositions containing the TACE-like protein of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a nontoxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a TACE-like or matrilysin-like protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3 untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1a

Expression and Purification of TACE-Like Protein in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp"") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6 X His tag") covalently linked to the carboxyl terminus of that polypeptide. However, in this example, the polypeptide coding sequence is inserted such that translation of the six His codons is prevented and, therefore, the polypeptide is produced with no 6 X His tag.

The DNA sequence encoding the desired portion of theTACE-like protein lacking the hydrophobic leader sequence is amplified from the deposited cDNA clone using PCR oligonucleotide primers which anneal to the amino terminal sequences of the desired portion of the TACE-like protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence: 5' CGC<u>CCATGG</u>CCCACGAAGGTTCTGAA 3' (SEQ ID NO:10) containing the underlined NcoI restriction site followed by 17 nucleotides complementary to the amino terminal coding sequence of the mature TACE-like sequence in FIG. 1. One of ordinary skill in the art would appreciate, of course, that the point in the protein coding sequence where the 5' primer begins may be varied to amplify a desired portion of the complete protein shorter or longer than the mature form. The 3' primer has the sequence: 5' CGC<u>AAGCTTT</u>CATTTGTAGGGCTGGTCTTTC 3' (SEQ ID NO:11) containing the underlined Hind III restriction site followed by 22 nucleotides complementary to the 3' end of the non-coding sequence in the TACE-like DNA sequence in FIG. 1.

The amplified TACE-like DNA fragments and the vector pQE60 are digested with NcoO and HindIII and the digested DNAs are then ligated together. Insertion of the TACE-like DNA into the restricted pQE60 vector places the TACE-like protein coding region including its associated stop codon downstream from the IPTG-inducible promoter and in-frame with an initiating AUG. The associated stop codon prevents translation of the six histidine codons downstream of the insertion point.

The ligation mixture is transformed into competent E. coli cells using standard procedures such as those described in Sambrook et al., Molecular Cloning: a Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing TACE-like protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4 C. in 6M guanidine-HCl, pH8. The cell debris is removed by centrifugation, and the supernatant containing the TACE-like protein is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure TACE-like protein. The purified protein is stored at 4 C. or frozen at −80 C.

Example 1b

Expression and Purification of Matrilysin-like Protein in E. coli

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp'") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6 X His tag") covalently linked to the carboxyl terminus of that polypeptide. However, in this example, the polypeptide coding sequence is inserted such that translation of the six His codons is prevented and, therefore, the polypeptide is produced with no 6 X His tag.

The DNA sequence encoding the desired portion of the matrilysin-like protein lacking the hydrophobic leader sequence is amplified from the deposited cDNA clone using PCR oligonucleotide primers which anneal to the amino terminal sequences of the desired portion of the matrilysin-like protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence: 5' CGC<u>CCATGG</u>CTGCAGACCATAAAGGATG 3' (SEQ ID NO:12) containing the underlined NcoI restriction site followed by 19 nucleotides complementary to the amino terminal coding sequence of the mature matrilysin-like sequence in FIG. 4. One of ordinary skill in the art would appreciate, of course, that the point in the protein coding sequence where the 5' primer begins may be varied to amplify a desired portion of the complete protein shorter or longer than the mature form.

The 3' primer has the sequence: 5' CGC <u>AAGCTT</u>CTCTAGTGCTTTCAGTTC 3' (SEQ ID NO:13) containing the underlined Hind III restriction site followed by 18 nucleotides complementary to the 3' end of the non-coding sequence in the matrilysin-like DNA sequence in FIG. 4.

The amplified matrilysin-like DNA fragments and the vector pQE60 are digested with NcoI and HindIII and the digested DNAs are then ligated together. Insertion of the matrilysin-like DNA into the restricted pQE60 vector places the matrilysin-like protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing matrilysin-like protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4 C. in 6M guanidine-HCl, pH8. The cell debris is removed by centrifugation, and the supernatant containing the matrilysin-like protein is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure matrilysin-like protein. The purified protein is stored at 4 C. or frozen at –80 C.

Example 2a

Cloning and Expression of TACE-Like Protein in a Baculovirus Expression System

In this illustrative example, the plasmid shuttle vector pA2 is used to insert the cloned DNA encoding the complete protein, including its naturally associated secretary signal (leader) sequence, into a baculovirus to express the mature TACE-like protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamrI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length TACE-like protein in the deposited clone, including the AUG initiation codon and the naturally associated leader sequence shown in FIG. 1 (SEQ ID NO:1), is amplified using PCR oligonucleotide primers corresponding to the 5' and 3' sequences of the gene.

The 5' primer has the sequence: 5' CGC GGATCCGCCATCATGTTCCTTCTCCTCGC 3' (SEQ ID NO:14) containing the underlined BamHI restriction enzyme site, an efficient signal for initiation of translation in eukaryotic cells, as described by Kozak, M., *J. Mol. Biol.* 196:947–950 (1987), followed by 17 bases (i.e., 22-38) of the sequence of the complete TACE-like protein shown in FIG. 1, beginning with the AUG initiation codon.

The 3' primer (full length) has the sequence: 5' CGC GGTACCACTACACAGGCAATGT 3' (SEQ ID NO: 15) containing the underlined, Asp718 restriction site followed by 16 nucleotides (i.e., 580–595) complementary to the 3' noncoding sequence in FIG. 1.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human TACE-like gene using the PCR method, in which one of the primers that is used to amplify the gene and the second primer is from well within the vector so that only those bacterial colonies containing the TACE-like gene fragment will show amplification of the DNA. The sequence of the cloned fragment is confirmed by DNA sequencing. This plasmid is designated herein pBacTACE-like.

Five μg of the plasmid pBacTACE-like is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 μg of BaculoGold™ virus DNA and 5 µg of the plasmid pBacTACE-like are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27 C. After 5 hours the transfection solution is removed from the plate and 1 ml of Grace's insect medium supplemented with 10% fetal calf serum is added. The plate is put back into an incubator and cultivation is continued at 27 C. for four days.

After four days the supernatant is collected and a plaque assay is performed, as described by Summers and Smith, supra. An agarose gel with "Blue Gal" (Life Technologies Inc., Gaithersburg, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., pages 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4 C. The recombinant virus is called V-TACE-like.

To verify the expression of the TACE-like gene, Sf9 cells are grown in Grace's medium supplemented with 10% heat inactivated FBS. The cells are infected with the recombinant baculovirus V-TACE-like at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 2b

Cloning and Expression of Matrilysin-like Protein in a Baculovirus Expression System In this illustrative example, the plasmid shuttle vector pA2 is used to insert the cloned DNA encoding the complete protein, including its naturally associated secretary signal (leader) sequence, into a baculovirus to express the mature matrilysin-like protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa califomica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length matrilysin-like protein in the deposited clone, including the AUG initiation codon and the naturally associated leader sequence shown in FIG. 4 (SEQ ID NO:4), is amplified using PCR oligonucleotide primers corresponding to the 5' and 3' sequences of the gene.

The 5' primer has the sequence: 5' CGC GGATCCGCCATCATGCAGCTCGTCATCTTA 3' (SEQ ID NO:16) containing the underlined BamHI restriction enzyme site, an efficient signal for initiation of translation in eukaryotic cells, as described by Kozak, M., *J. Mol. Biol.* 196:947–950 (1987), followed by 18 bases (i.e., 46–63) of the sequence of the complete matrilysin-like protein shown in FIG. 4, beginning with the AUG initiation codon.

The 3' primer (full length) has the sequence: 5' CGC GGTACCCTCTAGTGCTTTCAGTTC 3' (SEQ ID NO: 17) containing the underlined Asp718 restriction site followed by 18 nucleotides (i.e., 889–906) complementary to the 3' noncoding sequence in FIG. 4.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human matrilysin-like gene using the PCR method, in which one of the primers that is used to amplify the gene and the second primer is from well within the vector so that only those bacterial colonies containing the Matrilysin-like gene fragment will show amplification of the DNA. The sequence of the cloned fragment is confirmed by DNA sequencing. This plasmid is designated herein pBacmatrilysin-like.

Five µg of the plasmid pBacmatrilysin-like is co-transfected with 1.0 µg of a commercially available linearized baculovirus DNA ("BaculoGold™ baculovirus DNA", Pharmingen, San Diego, Calif.), using the lipofection method described by Feigner et al., *Proc. Natl. Acad. Sci. USA* 84:7413–7417 (1987). 1 μg of BaculoGod™ virus DNA and 5 μg of the plasmid pBacmatrilysin-like are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27 C. After 5 hours the transfection solution is removed from the plate and 1 ml of Grace's insect medium supplemented with 10% fetal calf serum is added. The plate is put back into an incubator and cultivation is continued at 27 C. for four days.

After four days the supernatant is collected and a plaque assay is performed, as described by Summers and Smith, supra. An agarose gel with "Blue Gal" (Life Technologies Inc., Gaithersburg, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., pages 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4 C. The recombinant virus is called V-matrilysin-like.

To verify the expression of the matrilysin-like gene, Sf9 cells are grown in Grace's medium supplemented with 10% heat inactivated FBS. The cells are infected with the recombinant baculovirus V-matrilysin-like at a multiplicity of infection ("MOI") of about 2. Six hours later the medium is removed and is replaced with SF900 II medium minus methionine and cysteine (available from Life Technologies, Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of TACE-Like and Matrilysin-Like Proteins in Mammalian Cells A typical mammalian expression vector contains the promoter element, which mediates the initiation of transcription of mRNA, the protein coding sequence, and signals required for the termination of transcription and polyadenylation of the transcript. Additional elements include enhancers, Kozak sequences, and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molec. Cell. Biol.* 5:438–447 (1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression of TACE-Like Protein in COS Cells

The expression plasmid, pTACE-like HA, is made by cloning a cDNA encoding TACE-like into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767–778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the TACE-like protein is cloned into the polylinker region of the vector so that recombinant protein expression is directed by the CMV promoter. The plasmid construction strategy is as follows. The TACE-like cDNA of the deposited clone is amplified using primers that contain convenient restriction sites, much as described above for construction of vectors for expression of TACE-like protein in E. coli. Suitable primers include the following, which are used in this example.

The 5' primer, containing the underlined BamHI site, a Kozak sequence, an AUG start codon and codons of the 5' coding region of the complete TACE-like protein has the following sequence: 5' CGC<u>GGATCC</u>GCCATCATGTTC CTTCTCCTCGC 3' (SEQ ID NO:14).

The 3' primer, containing the underlined XbaI site, a stop codon, and 16 bp (i.e., 580–595) of 3' coding sequence has the following sequence (at the 3' end): 5' CGC <u>TCTAGA</u>TCAAGCGTAGTCTGGGACGTCGTATGGGT AACTACACAGGCAATGT 3' (SEQ ID NO:18).

The PCR amplified DNA fragment and the vector, pcDNAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037), and the—transformed culture is plated on ampicillin media plates which then are incubated to allow growth of ampicillin resistant colonies. Plasmid DNA is isolated from resistant colonies and examined by restriction analysis or other means for the presence of the TACE-like-encoding fragment.

For expression of recombinant TACE-like protein, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TACE-like protein by the vector.

Expression of the TACE-like-HA fusion protein is detected by radiolabeling and immunoprecipitation, using methods described in, for example, Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 nM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression of TACE-Like Protein in CHO Cells

The vector pC4 is used for the expression of TACE-like protein. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357–1370 (1978); Hamlin, J. L. and Ma, C., *Biochem. et Biophys. Acta* 1097:107–143 (1990); Page, M. J. and Sydenham, M. A., *Biotechnology* 9:64–68 (1991). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human-actin promoter, the SV40 early or late promoters or the long terminal repeats from other retroviruses, e.g., HIV and HTLVI. Clontech's Tet-Off and Tet-On gene expression systems and similar systems can be used to express the TACE-like protein in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete TACE-like protein including its leader sequence is amplified using PCR oligonucleotide primers corresponding to the 5' and 3' sequences of the gene.

The 5' primer has the sequence 5' CGC <u>GGATCC</u>GCCATCATGTTCCTTCTCCTCGC 3' (SEQ ID NO:14) containing the underlined BamHI restriction enzyme site, an efficient signal for initiation of translation in eukaryotic cells, as described by Kozak, M., *J. Mol. Biol.* 196:947–950 (1987), followed by 17 bases (i.e., 22–38) of the sequence of the complete TACE-like protein shown in FIG. 1, beginning with the AUG initiation codon.

The 3' primer (full length) has the sequence: 5' CGC <u>GGTACC</u>ACTACACAGGCAATGT 3' (SEQ ID NO:15) containing the underlined, Asp718 restriction site followed by 16 nucleotides (i.e., 580–595) complementary to the 3' noncoding sequence in FIG. 1.

The amplified fragment is digested with the endonucleases BamHI and Asp718 and then purified again on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 3(c)

Cloning and Expression of Matrilysin-Like Protein in COS Cells

The expression plasmid, pmatrilysin-like HA, is made by cloning a cDNA encoding matrilysin-like into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767–778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the matrilysin-like protein is cloned into the polylinker region of the vector so that recombinant protein expression is directed by the CMV promoter. The plasmid construction strategy is as follows. The matrilysin-like cDNA of the deposited clone is amplified using primers that contain convenient restriction sites, much as described above for construction of vectors for expression of matrilysin-like protein in *E. coli*. Suitable primers include the following, which are used in this example.

The 5' primer, containing the underlined BamHI site, a Kozak sequence, an AUG start codon and codons of the 5' coding region of the complete matrilysin-like protein has the following sequence: 5' CGC<u>GGATCC</u>GCCATCATGCAG CTCGTCATCTTA 3' (SEQ ID NO:16).

The 3' primer, containing the underlined XbaI site, a stop codon, and 18 bp (i.e., 889–906) of 3' coding sequence has the following sequence (at the 3' end): 5' CGC <u>TCTAGA</u>TCAAGCGTAGTCTGGGACGTCGTATGGGT ACTCTAGTGCTTTCAGTTC 3' (SEQ ID NO:19).

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037), and the—transformed culture is plated on ampicillin media plates which then are incubated to allow growth of ampicillin resistant colonies. Plasmid DNA is isolated from resistant colonies and examined by restriction analysis or other means for the presence of the matrilysin-like-encoding fragment.

For expression of recombinant matrilysin-like protein, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of matrilysin-like protein by the vector.

Expression of the matrilysin-like-HA fusion protein is detected by radiolabeling and immunoprecipitation, using methods described in, for example, Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(d)

Cloning and Expression of Matrilysin-Like Protein in CHO Cells

The vector pC4 is used for the expression of matrilysin-like protein. Plasmid pC4 is described in detail above, in Example 3(b), which describes expression of TACE-like protein in CHO cells.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete matrilysin-like protein including its leader sequence is amplified using PCR oligonucleotide primers corresponding to the 5' and 3' sequences of the gene.

The 5' primer has the sequence 5' CGC <u>GGATCC</u>GCCATCATGCAGCTCGTCATCTTA 3' (SEQ ID NO:16) containing the underlined BamHI restriction enzyme site, an efficient signal for initiation of translation in eukaryotic cells, as described by Kozak, M., *J. Mol. Biol.* 196:947–950 (1987), followed by 18 bases (i.e.,46–63) of the sequence of the complete matrilysin-like protein shown in FIG. 4, beginning with the AUG initiation codon.

The 3' primer (full length) has the sequence: 5' CGC GGTACCCTCTAGTGCTTTCAGTTC 3' (SEQ ID NO: 17) containing the underlined, Asp718 restriction site followed by 18 nucleotides (i.e., 889–906) complementary to the 3' noncoding sequence in FIG. 4.

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 4a

Tissue distribution of TACE-Like mRNA Expression

Northern blot analysis is carried out to examine TACE-like gene expression in human tissues, using methods described by, among others, Sambrook et al., cited above. A cDNA probe containing the entire nucleotide sequence of the TACE-like protein (SEQ ID NO:1) is labeled with $^{32}P$ using the rediprime™ DNA labeling system (Amersham Life Science), according to manufacturer's instructions. After labeling, the probe is purified using a CHROMA SPIN- 100™ column (Clontech Laboratories, Inc.), according to manufacturer's protocol number PT 1200-1. The purified labeled probe is then used to examine various human tissues for TACE-like mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT 1190-1. Following hybridization and washing, the blots are mounted and exposed to film at −70 C. overnight, and films developed according to standard procedures.

Example 4(b)

Tissue Distribution of Matrilysin-Like Protein mRNA Expression

Northern blot analysis is carried out to examine matrilysin-like gene expression in human tissues, using methods described by, among others, Sambrook et al., cited above. A cDNA probe containing the entire nucleotide sequence of the matrilysin-like protein (SEQ ID NO:4) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for matrilysin-like mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70 C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a polynucleotide selected from the group consisting of:
   (a) a polynucleotide which encodes amino acid residues 1 to 182 of SEQ ID NO:2;
   (b) a polynucleotide which encodes amino acid residues 2 to 182 of SEQ ID NO:2;
   (c) a polynucleotide which encodes amino acid residues 16 to 182 of SEQ ID NO:2; and
   (d) a polynucleotide which is complementary to the polynucleotide of (a), (b), or (c).

2. The isolated nucleic acid molecule of claim 1 comprising a polynucleotide which encodes amino acid residues 16 to 182 of SEQ ID NO:2.

3. The isolated nucleic acid molecule of claim 2 comprising a polynucleotide which encodes amino acid residues 2 to 182 of SEQ ID NO:2.

4. The isolated nucleic acid molecule of claim 3 comprising a polynucleotide which encodes amino acid residues 1 to 182 of SEQ ID NO:2.

5. The isolated nucleic acid molecule of claim 1 wherein the polynucleotide is (a), (b), or (c).

6. A nucleic acid molecule comprising a polynucleotide which encodes an antigenic polypeptide having at least 50 contiguous amino acid residues of SEQ ID NO:2 wherein said polynucleotide is operably linked to a heterologous expression regulatory sequence.

7. An isolated nucleic acid molecule comprising a polynucleotide which encodes a polypeptide having tumor necrosis factor-alpha precursor cleavage activity wherein said polypeptide comprises at least 50 contiguous amino acid residues of SEQ ID NO. 2.

8. An isolated nucleic acid molecule comprising a polynucleotide which encodes a polypeptide selected from the group consisting of:
   (a) the antigenic polypeptide shown as amino acid residues 13 to 22 of SEQ ID NO:2;
   (b) the antigenic polypeptide shown as amino acid residues 31 to 46 of SEQ ID NO:2;
   (c) the antigenic polypeptide shown as amino acid residues 55 to 103 of SEQ ID NO:2;
   (d) the antigenic polypeptide shown as amino acid residues 123 to 151 of SEQ ID NO:2;
   (e) the antigenic polypeptide shown as amino acid residues 159 to 173 of SEQ ID NO:2: and
   (f) an antigenic polypeptide having at least 50 contiguous amino acid residues of SEQ ID NO:2.

9. A vector comprising the isolated nucleic acid molecule of claim 5.

10. A vector comprising the nucleic acid molecule of claim 6.

11. A vector comprising the nucleic acid molecule of claim 7.

12. A vector comprising the isolated nucleic acid molecule of claim 8.

13. A host cell comprising the vector of claim 9.

14. A host cell comprising the nucleic acid molecule of claim 6.

15. A host cell comprising the nucleic acid molecule of claim 7.

16. A host cell comprising the vector of claim 12.

17. A method of producing a TACE-like polypeptide comprising culturing the cell of claim 13 under conditions wherein the polypeptide is expressed and recovering the polypeptide.

18. A method of producing a TACE-like polypeptide comprising culturing the cell of claim 14 under conditions wherein the polypeptide is expressed and recovering the polypeptide.

19. A method of producing a TACE-like polypeptide comprising culturing the cell of claim 15 under conditions wherein the polypeptide is expressed and recovering the polypeptide.

20. A method of producing a TACE-like polypeptide comprising culturing the cell of claim 16 under conditions wherein the polypeptide is expressed and recovering the polypeptide.

21. An isolated nucleic acid molecule comprising a polynucleotide selected from the group consisting of:
  (a) a polynucleotide which encodes the full-length polypeptide encoded by the cDNA contained in ATCC Deposit No. 209042;
  (b) a polynucleotide which encodes the mature polypeptide encoded by the cDNA contained in ATCC Deposit No. 209042; and
  (c) a polynucleotide which is complementary to the polynucleotide of (a) or (b).

22. The isolated nucleic acid molecule of claim 21 comprising a polynucleotide which encodes the mature polypeptide encoded by the cDNA contained in ATCC Deposit No. 209042.

23. The isolated nucleic acid molecule of claim 22 comprising a polynucleotide which encodes the full-length polypeptide encoded by the cDNA contained in ATCC Deposit No. 209042.

24. The isolated nucleic acid molecule of claim 21 which further comprises a heterologous nucleic acid sequence.

25. The isolated nucleic acid molecule of claim 21 wherein the polynucleotide is (a) or (b).

26. A nucleic acid molecule comprising a polynucleotide which encodes an antigenic polypeptide having at least 50 contiguous amino acid residues of the polypeptide encoded by the cDNA contained in ATCC Deposit No. 209042 wherein said polynucleotide is operably linked to a heterologous expression regulatory sequence.

27. A vector comprising the isolated nucleic acid molecule of claim 25.

28. A vector comprising the nucleic acid molecule of claim 26.

29. A host cell comprising the vector of claim 27.

30. A host cell comprising the nucleic acid molecule of claim 26.

31. A method of producing a TACE-like polypeptide comprising culturing the cell of claim 29 under conditions wherein the polypeptide is expressed and recovering the polypeptide.

32. A method of producing a TACE-like polypeptide comprising culturing the cell of claim 30 under conditions wherein the polypeptide is expressed and recovering the polypeptide.

33. An isolated nucleic acid molecule comprising a polynucleotide selected from the group consisting of:
  (a) a polynucleotide which encodes amino acid residues 1 to 261 of SEQ ID NO:5;
  (b) a polynucleotide which encodes amino acid residues 2 to 261 of SEQ ID NO:5;
  (c) a polynucleotide which encodes amino acid residues 23 to 261 of SEQ ID NO:5; and
  (d) a polynucleotide which is complementary to the polynucleotide of (a), (b) or (c).

34. The isolated nucleic acid molecule of claim 33 comprising a polynucleotide which encodes amino acid residues 23 to 261 of SEQ ID NO:5.

35. The isolated nucleic acid molecule of claim 34 comprising a polynucleotide which encodes amino acid residues 2 to 261 of SEQ ID NO:5.

36. The isolated nucleic acid molecule of claim 35 comprising a polynucleotide which encodes amino acid residues 1 to 261 of SEQ ID NO:5.

37. The isolated nucleic acid molecule of claim 33 wherein the polynucleotide is (a), (b) or (c).

38. A nucleic acid molecule comprising a polynucleotide which encodes an antigenic polypeptide having at least 50 contiguous amino acid residues of SEQ ID NO:5 wherein said polynucleotide is operably linked to a heterologous expression regulatory sequence.

39. An isolated nucleic acid molecule comprising a polynucleotide which encodes a polypeptide selected from the group consisting of:
  (a) the antigenic polypeptide shown as amino acid residues 81 to 125 of SEQ ID NO:5;
  (b) the antigenic polypeptide shown as amino acid residues 141 to 167 of SEQ ID NO:5;
  (c) the antigenic polypeptide shown as amino acid residues 178 to 202 of SEQ ID NO:5; and
  (d) the antigenic polypeptide shown as amino acid residues 212 to 260 of SEQ ID NO:5.

40. A vector comprising the isolated nucleic acid molecule of claim 37.

41. A vector comprising the nucleic acid molecule of claim 38.

42. A vector comprising the isolated nucleic acid molecule of claim 39.

43. A host cell comprising the vector of claim 40.

44. A host cell comprising the nucleic acid molecule of claim 38.

45. A host cell comprising the vector of claim 42.

46. A method of producing a matrilysin-like polypeptide comprising culturing the cell of claim 43 under conditions wherein the polypeptide is expressed and recovering the polypeptide.

47. A method of producing a matrilysin-like polypeptide comprising culturing the cell of claim 44 under conditions wherein the polypeptide is expressed and recovering the polypeptide.

48. A method of producing a matrilysin-like polypeptide comprising culturing the cell of claim 45 under conditions wherein the polypeptide is expressed and recovering the polypeptide.

49. An isolated nucleic acid molecule comprising a polynucleotide selected from the group consisting of:
  (a) a polynucleotide which encodes the full-length polypeptide encoded by the cDNA contained in ATCC Deposit No. 209055;
  (b) a polynucleotide which encodes the mature polypeptide encoded by the cl)NA contained in ATCC Deposit No. 209055; and
  (c) a polynucleotide which is complementary to the polynucleotide of (a) or (b).

50. The isolated nucleic acid molecule of claim 49 comprising a polynucleotide which encodes the mature polypeptide encoded by the cDNA contained in ATCC Deposit No. 209055.

51. The isolated nucleic acid molecule of claim 50 comprising a polynucleotide which encodes the full-length polypeptide encoded by the cDNA contained in ATCC Deposit No. 209055.

52. The isolated nucleic acid molecule of claim 49 which further comprises a heterologous nucleic acid sequence.

53. The isolated nucleic acid molecule of claim 49 wherein the polynucleotide is (a) or (b).

54. A nucleic acid molecule comprising a polynucleotide which encodes an antigenic polypeptide having at least 50 contiguous amino acid residues of the polypeptide encoded by the cDNA contained in ATCC Deposit No. 209055 wherein said polynucleotide is operably linked to a heterologous expression regulatory sequence.

55. A vector comprising the isolated nucleic acid molecule of claim 53.

56. A vector comprising the nucleic acid molecule of claim 54.

57. A host cell comprising the vector of claim 55.

58. A host cell comprising the nucleic acid molecule of claim 54.

59. A method of producing a matrilysin-like polypeptide comprising culturing the cell of claim 57 under conditions wherein the polypeptide is expressed and recovering the polypeptide.

60. A method of producing a matrilysin-like polypeptide comprising culturing the cell of claim 58 under conditions wherein the polypeptide is expressed and recovering the polypeptide.

* * * * *

UNITED STATES PATENT AND TRADEMARK OFFICE
CERTIFICATE OF CORRECTION

PATENT NO. : 6,046,031 Page 1 of 1
DATED : April 4, 2000
INVENTOR(S) : Jian Ni, Steve Ruben, Laurie Brewer, Reiner Gentz and Craig Rosen It is certified that error appears in the above-identified patent and that said Letters Patent is hereby corrected as shown below:

<u>Column 58,</u>
Line 48, please remove "cl)NA" and replace it with -- cDNA --.

Signed and Sealed this

Fourth Day of June, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 704 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ACGAGGCGCT CTGGCTGAGC CATGTTCCTT CTCCTCGCCC TCCTCACTGA GCTTGGAAGA      60

CTGCAAGCCC ACGAAGGTTC TGAAGGAATA TTTCTGCATG TCACAGTTCC ACGGAAGATT     120

AAGTCAAATG ACAGTGAAGT TCAGAGAGG AAGATGATTT ACATCATTAC AATTGATGGA      180

CAACCTTACA CTCTACATCT CGGAAAACAA TCATTCTTAC CCCAGAACTT TTTGGTTTAT     240

ACATATAATG AAACTGGATC TTTGCATTCT GTGTCTCCAT ATTTTATGAT GCATTGCCAT     300

TACCAAGGAT ATGCTGCCGA ATTTCCAAAT TCATTTGTGA CACTCAGTAT ATGTTCTGGT     360

CTCAGGGGAT TTCTCCAGTT TGAAAATATC AGTTATGGAA TTGAACCAGT AGAATCTTCA     420

GCAAGATTTG AGCATATAAT TTATCAAATG AAAAATAATG ATCCAAATGT ATCCATTTTA     480

GCAGTAAATT ACAGTCATAT TTGGCAGAAA GACCAGCCCT ACAAAGTTCC TTTAAACTCA     540

CAGGTGACTG TCATCATTCT GATGTTATGA CATACTAGAA CATTGCCTGT GTAGTTTTCT     600

TGTAAATCAT GAAAGGAATT TAGTTAGCTG TTGAGTAGGA ATATTAAATT TTATGTATTT     660

TTCTACCTTT AAATAAAACA TTGAAACTTC AAAAAAAAAA AAAA                      704
```

(2) INFORMATION FOR SEQ ID NO:2:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Phe Leu Leu Leu Ala Leu Leu Thr Glu Leu Gly Arg Leu Gln Ala
 1               5                  10                  15

His Glu Gly Ser Glu Gly Ile Phe Leu His Val Thr Val Pro Arg Lys
            20                  25                  30

Ile Lys Ser Asn Asp Ser Glu Val Ser Glu Arg Lys Met Ile Tyr Ile
        35                  40                  45

Ile Thr Ile Asp Gly Gln Pro Tyr Thr Leu His Leu Gly Lys Gln Ser
    50                  55                  60

Phe Leu Pro Gln Asn Phe Leu Val Tyr Thr Tyr Asn Glu Thr Gly Ser
65                  70                  75                  80

Leu His Ser Val Ser Pro Tyr Phe Met Met His Cys His Tyr Gln Gly
                85                  90                  95

Tyr Ala Ala Glu Phe Pro Asn Ser Phe Val Thr Leu Ser Ile Cys Ser
            100                 105                 110

Gly Leu Arg Gly Phe Leu Gln Phe Glu Asn Ile Ser Tyr Gly Ile Glu
        115                 120                 125

Pro Val Glu Ser Ser Ala Arg Phe Glu His Ile Ile Tyr Gln Met Lys
    130                 135                 140

Asn Asn Asp Pro Asn Val Ser Ile Leu Ala Val Asn Tyr Ser His Ile
145                 150                 155                 160

Trp Gln Lys Asp Gln Pro Tyr Lys Val Pro Leu Asn Ser Gln Val Thr
                165                 170                 175

Val Ile Ile Leu Met Leu
            180
```

(2) INFORMATION FOR SEQ ID NO:3:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Phe Leu Leu Leu Val Leu Leu Thr Gly Leu Gly Gly Met His Ala
1               5                  10                  15

Asp Leu Asn Pro His Lys Thr Phe Leu Gln Thr Thr Ile Pro Glu Lys
            20                  25                  30

Ile Ser Ser Ser Asp Ala Lys Thr Asp Pro Glu His Asn Val Val Tyr
        35                  40                  45

Met Ile Thr Ile Glu Gly Lys Pro Tyr Phe Val His Leu Lys Lys Gln
    50                  55                  60

Ser Ile Leu Ser Ser Ala Ser Phe Ile His Ser Tyr Asp Lys Asn Asp
65                  70                  75                  80

Ile Arg His Ser Lys Pro Leu Leu Val Gln Met Asp Cys Asn Tyr Asn
                85                  90                  95

Gly Tyr Val Ala Gly Ile Pro Asn Ser Leu Val Thr Leu Ser Val Cys
            100                 105                 110

Ser Gly Leu Arg Gly Thr Met Gln Leu Lys Asn Ile Ser Tyr Gly Ile
        115                 120                 125

Glu Pro Met Glu Ala Val Ser Gly Phe Ile His Lys Ile Tyr Glu Glu
    130                 135                 140

Lys Phe Ala Asp Thr Asn Ile Leu Leu Glu Glu Asn Asp Thr Tyr Ser
145                 150                 155                 160

Trp Phe Asn Ser Glu Tyr Gln Val Arg Lys Ser Ser Glu Lys Thr Asp
                165                 170                 175

Phe Ile Lys Leu Phe
            180
```

(2) INFORMATION FOR SEQ ID NO:4:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CCAAGCTCGA AATTAACCCT CACTAAAGGG AACAAAGGCA CGAGCATGCA GCTCGTCATC      60

TTAAGAGTTA CTATCTTCTT GCCCTGGTGT TTCGCCGTTC CAGTGCCCCC TGCTGCAGAC     120

CATAAAGGAT GGGACTTTGT TGAGGGCTAT TTCCATCAAT TTTTCCTGAC CGAGAAGGAG     180

TCGCCACTCC TTACCCAGGA GACACAAACA CAGCTCCTGC AACAATTCCA TCGGAATGGG     240

ACAGACCTAC TTGACATGCA GATGCATGCT CTGCTACACC AGCCCCACTG TGGGGTGCCT     300

GATGGGTCCG ACACCTCCAT CTCGCCAGGA AGATGCAAGT GGAATAAGCA CACTCTAACT     360

TACAGGATTA TCAATTACCC ACATGATATG AAGCCATCCG CAGTGAAAGA CAGTATATAT     420

AATGCAGTTT CCATCTGGAG CAATGTGACC CCTTTGATAT TCCAGCAAGT GCAGAATGGA     480

GATGCAGACA TCAAGGTTTC TTTCTGGCAG TGGGCCCATG AAGATGGTTG GCCCTTTGAT     540
```

```
GGGCCAGGTG GTATCTTAGG CCATGCCTTT TTACCAAATT CTGGAAATCC TGGAGTTGTC      600

CATTTTGACA AGAATGAACA CTGGTCAGCT TCAGACACTG GATATAATCT GTTCCTGGTT      660

GCAACTCATG AGATTGGGCA TTCTTTGGGC CTGCAGCACT CTGGGAATCA GAGCTCCATA      720

ATGTACCCCA CTTACTGGTA TCACGACCCT AGAACCTTCC AGCTCAGTGC CGATGATATC      780

CAAAGGATCC AGCATTTGTA TGGAGAAAAA TGTTCATCTG ACATACCTTA ATGTTAGCAC      840

AGAGGACTTA TTCAACCTGT CTTTCAGGGA GTTTATTGGA GGATCAAAGA ACTGAAAGCA      900

CTAGAGCAGC CTTGGGGACT GCTAGGATGA AGCCCTAAAG AATGCAACCT AGTCAGGTTA      960

GCTGAACCGA CACTCAAAAC GCTACTGAGT CACAATAAAG ATTGTTTTAA AGAGTAAAAA     1020

AAAAAAAAAA AAAAA                                                     1035
```

(2) INFORMATION FOR SEQ ID NO:5:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Gln Leu Val Ile Leu Arg Val Thr Ile Phe Leu Pro Trp Cys Phe
1               5                   10                  15

Ala Val Pro Val Pro Pro Ala Ala Asp His Lys Gly Trp Asp Phe Val
                20                  25                  30

Glu Gly Tyr Phe His Gln Phe Phe Leu Thr Glu Lys Glu Ser Pro Leu
            35                  40                  45

Leu Thr Gln Glu Thr Gln Thr Gln Leu Leu Gln Gln Phe His Arg Asn
        50                  55                  60

Gly Thr Asp Leu Leu Asp Met Gln Met His Ala Leu Leu His Gln Pro
65                  70                  75                  80

His Cys Gly Val Pro Asp Gly Ser Asp Thr Ser Ile Ser Pro Gly Arg
                85                  90                  95

Cys Lys Trp Asn Lys His Thr Leu Thr Tyr Arg Ile Ile Asn Tyr Pro
                100                 105                 110

His Asp Met Lys Pro Ser Ala Val Lys Asp Ser Ile Tyr Asn Ala Val
            115                 120                 125

Ser Ile Trp Ser Asn Val Thr Pro Leu Ile Phe Gln Gln Val Gln Asn
        130                 135                 140

Gly Asp Ala Asp Ile Lys Val Ser Phe Trp Gln Trp Ala His Glu Asp
145                 150                 155                 160

Gly Trp Pro Phe Asp Gly Pro Gly Gly Ile Leu Gly His Ala Phe Leu
                165                 170                 175

Pro Asn Ser Gly Asn Pro Gly Val Val His Phe Asp Lys Asn Glu His
            180                 185                 190

Trp Ser Ala Ser Asp Thr Gly Tyr Asn Leu Phe Leu Val Ala Thr His
        195                 200                 205

Glu Ile Gly His Ser Leu Gly Leu Gln His Ser Gly Asn Gln Ser Ser
210                 215                 220

Ile Met Tyr Pro Thr Tyr Trp Tyr His Asp Pro Arg Thr Phe Gln Leu
225                 230                 235                 240
```

-continued

```
Ser Ala Asp Asp Ile Gln Arg Ile Gln His Leu Tyr Gly Glu Lys Cys
                245                 250                 255

Ser Ser Asp Ile Pro
            260

(2) INFORMATION FOR SEQ ID NO:6:

(i) SEQUENCE CHARACTERISTICS:
        (A) LENGTH: 264 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
                20                  25                  30

Glu Gln Ala Gln Asp Tyr Leu Lys Arg Phe Tyr Leu Tyr Asp Ser Glu
            35                  40                  45

Thr Lys Asn Ala Asn Ser Leu Glu Ala Lys Leu Lys Glu Met Gln Lys
        50                  55                  60

Phe Phe Gly Leu Pro Ile Thr Gly Met Leu Asn Ser His Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
                100                 105                 110

Ile Val Ser Tyr Thr Arg Asp Leu Pro His Ile Thr Val Asp Arg Leu
            115                 120                 125

Val Ser Lys Ala Leu Asn Met Trp Gly Lys Glu Ile Pro Leu His Phe
        130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
                180                 185                 190

Asp Glu Asp Glu Arg Trp Thr Asp Gly Ser Ser Leu Gly Ile Asn Phe
            195                 200                 205

Leu Tyr Ala Ala Thr His Glu Leu Gly His Ser Leu Gly Met Gly His
        210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser
            260

(2) INFORMATION FOR SEQ ID NO:7:

(i) SEQUENCE CHARACTERISTICS:
        (A) LENGTH: 506 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:7:

| | | | | | |
|---|---|---|---|---|---|
| AATTCGGCAC | GAGGCGCTCT | GGCTGAGCCA | TGTTCCTTCT | CCTCGCCCTC | CTCACTGAGC | 60 |
| TTGGAAGACT | GCAAGCCCAC | GAAGGTTCTG | AAGGAATATT | TCTGCATGTC | ACAGTTCCAC | 120 |
| GGAAGATTAA | GTCAAATGAC | AGTGAAGTTT | CAGAGAGGAA | GATGATTTAC | ATCATTACAA | 180 |
| TTGATGGACA | ACCTTACACT | CTACATCTCG | GAAAACAATC | ATTCTTACCC | CAGAACTTTT | 240 |
| TGGTTTATAC | ATATAATGAA | ACTGGATCTT | TGCATTCTGT | GTCTCCATAT | TTTATGATGC | 300 |
| ATTGCCATTA | CCAAGGGATA | TGCTGCCGAA | TNTTCCAANT | TTCATTTGNG | ACACTCAGTA | 360 |
| TATGGTNCTG | GNCTCAGGTT | AAAAAATCTT | TTCAAAATTT | TTACCCCNAT | ANTCTGGAAA | 420 |
| TATACATTNT | AGTGGGAAAG | NTTNTGTATG | GTTANATGGG | TCTGGAANTG | ATGGNGTAAC | 480 |
| ACAAANANTT | NTCCNGGNTA | TTGGGT | | | | 506 |

(2) INFORMATION FOR SEQ ID NO:8:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| AAATGAGGGT | TTGGCATGCA | GCTCGTCATC | TTAAGAGTTA | CTATCTTCTT | GCCCTGGTGT | 60 |
| TTCGCCGTTC | CAGTGCCCCC | TGCTGCAGAC | CATAAAGGAT | GGGACTTTGT | TGAGGGCTAT | 120 |
| TTCCATCAAT | TTTTCCTGAC | CGAGAAGGAG | TCGCCACTCC | TTACCCAGGA | GACACAAACA | 180 |
| CAGCTCCTGC | AACAATTCCA | TCGGAATGGG | ACAGACCTAC | TTGACATGCA | GATGCATGCT | 240 |
| TCTGCTACAN | CAGCCCCACT | GTGGGGTGCC | TGATGGGTCC | GACAACTNCA | TCTCGCCAGG | 300 |
| AAGATGCAAG | TGGATTAAGC | ACA | | | | 323 |

(2) INFORMATION FOR SEQ ID NO:9:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| GACAAATNAG | GGTTTGGNAT | GCAGCTCGTC | ATCTTAAGAG | TTACTATCTT | CTTGCCCTGG | 60 |
| TGTTTCGCCG | TTCCAGTGCC | CCCTGCTGCA | GACCATAAAG | GATGGGACTT | TGTTGAGGGC | 120 |
| TATTTCCATC | AATTTTTCCT | GACCGAGAAG | GAGTCGCCAC | TCCTTACCCA | GGAGACACAA | 180 |
| ACACAGCTCC | TGCAACAATT | CCATCGGAAT | GGGACAGACC | TACTTGACAT | GCAGT | 235 |

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCCCATGGC CCACGAAGGT TCTGAA                                                    26

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCAAGCTTT CATTTGTAGG GCTGGTCTTT C                                              31

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCCCATGGC TGCAGACCAT AAAGGATG                                                  28

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCAAGCTTC TCTAGTGCTT TCAGTTC                                                   27

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGATCCG CCATCATGTT CCTTCTCCTC GC                                             32

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGCGGTACCA CTACACAGGC AATGT                                              25

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGCGGATCCG CCATCATGCA GCTCGTCATC TTA                                     33

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGCGGTACCC TCTAGTGCTT TCAGTTC                                            27

(2) INFORMATION FOR SEQ ID NO:18:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGCTCTAGAT CAAGCGTAGT CTGGGACGTC GTATGGGTAA CTACACAGGC AATGT             55

(2) INFORMATION FOR SEQ ID NO:19:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGCTCTAGAT CAAGCGTAGT CTGGGACGTC GTATGGGTAC TCTAGTGCTT TCAGTTC           57

(2) INFORMATION FOR SEQ ID NO:20:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AGGAAATGAG GGTTTGGCAT GCAGCTCGTC ATCTTAAGAG TTACTATCTT CTTGCCCTGG        60

-continued

```
TGTTTCGCCG TTCCAGTGCC CCCTGCTGCA GACCATAAAG GATGGGACTT TGTTGAGGGC      120

TATTTCCATC AATTTTTCCT GACCGAGAAG GAGTCGCCAC TCCTTACCCA GGAGACACAA      180

ACACAGCTCC TGCAACAATT CCATCGGAAT GGGACAGACC TACTTGACAT GCAGATGCAT      240

GCTCTGCTAC ACCAGCCCCA CTGTGGGGTG CCTGATGGGT CCGACACTCC ATCTCGCCAG      300

GAAGATGCAA GTGGAATAAG CACACTCTAA CTTACAGGAT TATCAATTAC CCACATGATA      360

TGAAGCCATC CGCAGTGAAA GACAGTATAT ATAATGCAGT TTCCATCTGG AGCAATGTGA      420

CCCCTTTGAT ATTCCAGCAA GTGCAGAATG GAGATGCAGA CATCAAGGTT TCTTTCTGGC      480

AGTGGGCCCA TGAAGATGGT TGCCCTTTGA TGGGCCAGGT GGTATCTTAG GCCATGCCTT      540

TTTACCAAAT TCTGGAAATC CTGGAGTTGT CCATTTTGAC AAGAATGAAC ACTGGTCAGC      600

TTCAGACACT GGATATAATC TGTTCCTGGT TGCAACTCAT GAGATTGGGC ATTCTTTGGG      660

CCTGCAGCAC TCTGGGAATC AGAGCTCCAT AATGTACCCC ACTTACTGGT ATCACGACCC      720

TAGAACCTTC CAGCTCAGTG CCGATGATAT CCAAAGGATC CAGCATTTGT ATGGAGAAAA      780

ATGTTCATCT GACATACCTT AATGTTAGCA CAGAGGACTT ATTCAACCTG TCCTTTCAGG      840

GAGTTTATTG GAGGATCAAA GAACTGAAAG CACTAGAGCA GCCTTGGGGA CTGCTAGGAT      900

GAAGCCCTAA AGAATGCAAC CTAGTCAGGT TAGCTGAACC GACACTCAAA ACGCTACTGA      960

GTCACAATAA AGATTGTTTT AAAGAGTAAA AAAAAAAAAA AAAAACTCGA               1010
```